US012708084B2

(12) United States Patent
Brown et al.

(10) Patent No.: US 12,708,084 B2
(45) Date of Patent: Aug. 18, 2026

(54) PEANUT VARIETY 'GEORGIA-SP/RKN'

(71) Applicant: University of Georgia Research Foundation, Inc., Athens, GA (US)

(72) Inventors: I. Nino Brown, Tifton, GA (US); William Branch, Tifton, GA (US); Tim Brenneman, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 518 days.

(21) Appl. No.: 18/120,837

(22) Filed: Mar. 13, 2023

(65) Prior Publication Data

US 2024/0306583 A1 Sep. 19, 2024

(51) Int. Cl.
*A01H 6/54* (2018.01)
*A01H 5/10* (2018.01)

(52) U.S. Cl.
CPC ............... *A01H 6/541* (2018.05); *A01H 5/10* (2013.01)

(58) Field of Classification Search
None
See application file for complete search history.

(56) References Cited

U.S. PATENT DOCUMENTS 11,197,449 B2 * 12/2021 Branch .................... A01H 5/10

OTHER PUBLICATIONS

Brown et al. Registration of 'Georgia-SP/RKN' peanut. (2023) J. Plant Regist.; vol. 17; pp. 47-55 (Year: 2023).*

* cited by examiner

*Primary Examiner* — Cathy Kingdon
(74) *Attorney, Agent, or Firm* — Thomas | Horstemeyer LLP.

(57) ABSTRACT

Herein provided is a new runner-type peanut variety designated 'Georgia-SP/RKN' as well as the seeds, plants and derivatives of the new peanut variety 'Georgia-SP/RKN'. Methods for producing peanut plants by crossing the new peanut variety 'Georgia-SP/RKN' with itself or another peanut variety (such as another spanish, valencia, virginia, or runner-type peanut variety) and plants produced by such methods are also provided. 'Georgia-SP/RKN' is a unique spanish market-type peanut cultivar having a combination of a high level of resistance to peanut root-knot nematode (RKN) (*Meloidogyne arenaria*) and a high level of resistance to tomato spotted wilt virus (TSWV), high yield and high-oleic fatty acid content of seed oil. 'Georgia-SP/RKN' provides a medium plus maturity spanish market-type peanut cultivar with intermediate decumbent runner growth habit, tan testa color, and large spanish market-type seed size.

19 Claims, 1 Drawing Sheet

Chromosome A09

Georgia-14N

Georgia-SP/RKN

Georgia-06G

PEANUT VARIETY 'GEORGIA-SP/RKN'

FIELD

This disclosure provides a new and distinctive peanut variety, 'Georgia-SP/RKN', which is a high-oleic spanish market-type peanut that is resistant to tomato spotted wilt caused by Tomato Spotted Wilt Virus (TSWV) and peanut root-knot nematode [*Meloidogyne arenaria* (Neal)] (RKN).

BACKGROUND

The peanut is an annual herbaceous plant of the legume family. Originally cultivated in South America and the eastern slopes of the Andes mountains, peanuts are grown worldwide in the tropic and temperate zones and is a major oilseed crop and rich source of protein.

There are four U.S. peanut market types (runner, virginia, spanish, and valencia). The runner-type, as well as the virginia-type, are classified as (*A. hypogaea* subspecies *hypogaea* var. *hypogaea*), valencia-type (*A. fastigiata* var. *fastigiata*) and spanish-type (*A. hypogaea* subsp. *fastigiata* var. *vulgaris*). Peanuts in the runner-type market class are the most commonly used varieties and are found in diverse products such as peanut butter, salted nuts, and confectionery products. On the other hand, peanut varieties in the virginia market class are largely used as salted nuts and in-shell market. The valencia is largely used in peanut butter, while the spanish type is used in certain niche markets where small round peanuts are needed, such as confectionery products and red skin peanuts.

Peanut is an important and valuable oilseed crop and a rich source of protein. In the United States, peanuts are primarily utilized as whole seeds for human foods such as peanut butter, roasted seeds, and confections. Peanuts are rich in nutrients, providing over 30 essential nutrients and phytonutrients, and are a good source of niacin, folate, fiber, magnesium, vitamin E, manganese and phosphorus. They are also naturally free of trans-fats and sodium, and contain about 25% protein.

Peanut is particularly susceptible to viruses and fungi as well as various pests during growth and storage. Indeed, diseases and pests are major constraints to peanut production worldwide, including spotted wilt caused by the pathogen Tomato Spotted Wilt Virus (TSWV) and peanut root-knot nematode (RKN) caused by the pathogen *Meloidogyne arenaria*. Peanut varieties resistant to such pathogens and insects are needed.

SUMMARY

The present disclosure relates to a new peanut variety, 'Georgia-SP/RKN'. This new variety is a high-yielding, high-oleic, peanut root-knot nematode [*Meloidogyne arenaria* (Neal)] (RKN) resistant, and Tomato spotted wilt virus (TSWV) resistant, large-seeded, spanish market-type peanut (*Arachis hypogaea* L. subsp. *hypogaea* var. *hypogaea*) cultivar developed in Tifton, GA. 'Georgia-SP/RKN' was derived from an individual plant selection made from the cultivar 'Georgia-17SP'. Details on the breeding history of 'Georgia-17SP' and 'Georgia-SP/RKN') are found in Example 1 and Table A. below. Briefly, 'Georgia-17SP' was derived from a cross between 'Georgia-02C' and an $F_4$ selection from a population developed by crossing 'Georgia-01R' and 'COAN' (parentage of 'Georgia-17SP' referred to as "Georgia-02C/Georgia-01R/COAN"). Pedigree selection was carried out on individual plants within the $F_2$, $F_3$, and $F_4$ generation from the cross of Georgia-02C/Georgia-01R/COAN and was released as a pure-line as 'Georgia-17SP'. In 2016, RKN resistant individual plant selections of 'Georgia-17SP' were made in RKN-infested field trials. Plants were given experimental designation GA 082549R-2 and tested in replicated yield trials carried out in 2018-2021 over multilocation plots in Georgia. Visual evaluations were made to confirm stability of RKN resistance in both nematode-free and infested locations, and DNA-marker screening was performed to confirm presence of RKN resistance genes. GA-082549R-2 was designated 'Georgia-SP/RKN'. 'Georgia-SP/RKN' demonstrated significantly higher RKN resistance than 'Georgia-17SP'. 'Georgia-SP/RKN' is most similar to 'Georgia-17SP' except that 'Georgia SP/RKN' has a very high level of RKN-resistance, and should be an excellent cultivar for a high-oleic option in the U.S. peanut production area. 'Georgia-SP/RKN' has no genetically modified organisms (GMO) in its ancestry.

A deposit of seeds of the new peanut variety 'Georgia-SP/RKN' made on May 12, 2023 with the American Type Culture Collection (ATCC), 10801 University Blvd., Manassas, VA, 20110 under Accession No. PTA-127584 is intended to meet all of the requirements of 37 C.F.R. §§ 1.801-1.809. The deposit will be maintained in the depository for a period of 30 years, or 5 years after the last request, or for the effective life of the patent, whichever is longer, and will be replaced, if necessary, during that period. A deposit of 5000 seeds of 'Georgia-SP/RKN' was made to the U.S. National Plant Germplasm System (NPGS) in September 2022 under PI No. 700991. In one embodiment, the disclosure provides peanut seed deposited as ATCC Accession No. PTA-127584 (NPGS PI No. PI #700991), as well as bulk peanut seed containing such seeds.

The disclosure provides peanut plants having or consisting of the morphological and physiological characteristics of 'Georgia-SP/RKN', such as the characteristics noted in Examples 2-11 and/or Tables 1-11, for example high resistance to RKN caused by *Meloidogyne arenaria*, TSWV resistance, high percentage of total sound mature kernels (TSMK), high pod yield, small percentage of large fancy pods (e.g., 13.49 mm size distribution), high percentage of total meat content, medium-plus maturity (e.g., about 147-150 days to maturity in south Georgia), runner-type growth and branching habit, large spanish-type seed size, tan seedcoat (testa) color, or combination thereof.

In some examples, a 'Georgia-SP/RKN' plant or progeny thereof has a lower TSWV and RKN counts than other similar cultivars. For instance, 'Georgia-SP/RKN' can have a mid-season TSWV susceptibility of about 5% or less, about 4% or less, about 2% or less, and the like, which will vary somewhat across seasons and in different environments. In embodiments, 'Georgia-SP/RKN' exhibited a mid-season TSWV susceptibility of 1.8 to 4.2% over 4 trials grown in 2 years; late season total disease count ranged from 1.2 to 6.8% over 4 trials grown in 2 years. Susceptibility to TSWV and late season total disease was significantly lower than most spanish market-type cultivars tested (Table 3 & 4).

Leaf scorch or pepper spot disease symptoms caused by the fungus *Leptosphaerulina crassiasca* (Sechet) Jackson and Bell, is primarily a cosmetic issue. Leaf scorch symptom ratings were higher in Georgia-SP/RKN (6.6) compared to Georgia-17SP (4.4), a closely related line, and could potentially be used as a diagnostic for identification. Root-knot nematode resistance as measured by RKN count (number of J2 stage root-knot nematodes in 100 $cm^3$ soil) was less than similar cultivars. In embodiments, the RKN count ranged from 0 to 57, whereas susceptible check cultivars ranged from 93 to 867 RKN count in 2 trials grown in 2019 (Table 10). Visual gall ratings, a percentage of obviously infected tissue for roots and pods indicated root galling of 0 to 0.3% for Georgia-SP/RKN, lower than the comparison cultivars which ranged from 6.5 to 53.3% (Table 10). Pod galling in Georgia-SP/RKN was also reduced with pod galling of 0% compared to the susceptible cultivars with 10.5 and 60.0%. Thus, in embodiments, Georgia-SP/RKN plants of the preset disclosure have an RKN count of about 100 or less and/or an RKN visual gall rating of about 5% or less, about 2% or less, about 1% or less, about 0.5% or less, and the like.

Also provided are seeds of such plants, progeny of such plants, and parts of such plants (such as pollen, ovules and cells). In one example, the disclosure provides peanut plants having the genotype of 'Georgia-SP/RKN'. For example, the disclosure provides plants produced by growing the seed of the new peanut variety 'Georgia-SP/RKN'.

The disclosure describes a tissue culture of regenerable cells of the new peanut variety 'Georgia-SP/RKN' from the seeds of 'Georgia-SP/RKN' as described above, as well as plants regenerated therefrom. Such regenerated peanut plants can include or consist of the physiological and morphological characteristics of a plant grown from the seed of the new peanut variety 'Georgia-SP/RKN'. Exemplary regenerable cells include but are not limited to those from protoplasts or cells, such as those from embryos, meristematic cells, pollen, leaves, roots, root tips, anther, pistil, flower, seed, cotyledon, hypocotyl, shoot, pedicel, petiole, or stem of the new peanut variety 'Georgia-SP/RKN'.

Methods of producing peanut seed from the 'Georgia-SP/RKN' peanut plants are provided. In some examples such methods include crossing 'Georgia-SP/RKN' with itself or a second peanut plant and harvesting a resulting peanut seed. In some examples, the second peanut plant has one or more desirable traits, which is/are introduced into (e.g., via transformation) plants and seeds resulting from such a cross. For example, the second plant can be transgenic, wherein the transgene confers the desirable trait(s). Seeds produced by such methods, including $F_1$ hybrid seeds, as well as peanut plants or parts thereof produced by growing such a seed, are provided. In some examples, the method of crossing includes planting seeds of the new peanut variety 'Georgia-SP/RKN', cultivating peanut plants resulting from the seeds until the plants bear flowers, allowing fertilization of the flowers of the plants; and harvesting seeds produced from the plants.

Methods are provided for producing a plant of peanut variety 'Georgia-SP/RKN' that has one or more added desired traits, as well as plants and seeds generated from such methods. In one example, such a method provides a peanut plant having a single locus conversion of the new peanut variety 'Georgia-SP/RKN', wherein the peanut plant includes or expresses the physiological and morphological characteristics of the new peanut variety 'Georgia-SP/RKN' (such as those shown in Tables 2-10). In some embodiments, the single locus conversion can include a dominant or recessive allele. Such methods can include introducing a transgene that confers one or more desired traits into a plant of the new peanut variety 'Georgia-SP/RKN' (e.g., via transformation). Exemplary desired traits include herbicide tolerance, resistance to an insect, resistance to a bacterial disease, resistance to a viral disease, resistance to a fungal disease, resistance to a nematode, resistance to a pest, male sterility, site-specific recombination; abiotic stress tolerance (such as tolerance to drought, heat, cold, low or high soil pH level, and/or salt); modified phosphorus content, modified antioxidant content, modified essential seed amino acid content, modified fatty acid content, modified carbohydrate content, and modified peanut fiber content, modified oil content, modified protein content, or other improved nutritional qualities.

Methods of introducing a single locus conversion (such as a desired trait) into the new peanut variety 'Georgia-SP/RKN' are provided. In some examples the methods include (a) crossing a plant of variety 'Georgia-SP/RKN' with a second plant having one or more desired traits to produce $F_1$ progeny plants; (b) selecting $F_1$ progeny plants that have the desired trait to produce selected $F_1$ progeny plants; (c) crossing the selected progeny plants with at least a first plant of variety 'Georgia-SP/RKN' to produce backcross progeny plants; (d) selecting backcross progeny plants that have the desired trait and physiological and morphological characteristics of peanut variety 'Georgia-SP/RKN' to produce selected backcross progeny plants; and (e) repeating steps (c) and (d) one or more times in succession to produce selected second or higher backcross progeny plants that include the desired trait and the physiological and morphological characteristics of peanut variety 'Georgia-SP/RKN' when grown in the same environmental conditions. In some embodiments, the single locus confers a desirable trait, such as herbicide tolerance, resistance to an insect, resistance to a bacterial disease, resistance to a viral disease, resistance to a fungal disease, resistance to a nematode, resistance to a pest, male sterility, site-specific recombination; abiotic stress tolerance (such as tolerance to drought, heat, low or high soil pH level, and/or salt), modified phosphorus content, modified antioxidant content; modified essential seed amino acid content, modified fatty acid content, modified carbohydrate content, modified peanut fiber content, low pod-splitting, modified seed yield, modified oil percent, modified protein percent, modified fancy pod percent, modified pod size, modified pod shape, and/or modified pod color. In some examples, the single locus confers the ability to synthesize a protein encoded by a gene located within the single locus.

Methods of producing a peanut plant derived from the new peanut variety 'Georgia-SP/RKN', such as an inbred peanut plant, are provided. In particular examples the method includes (a) preparing a progeny plant derived from the new peanut variety 'Georgia-SP/RKN' by crossing a plant of 'Georgia-SP/RKN' with a peanut plant of a second variety; and (b) crossing the progeny plant with itself or a second plant to produce a progeny plant of a subsequent generation which is derived from a plant of the new peanut variety 'Georgia-SP/RKN'. In some embodiments, the method further includes (c) growing a progeny plant of a subsequent generation from said seed and crossing the progeny plant of a subsequent generation with itself or a second plant; and (d) repeating steps (b) and (c) for at least 2 additional generations (such as at least 3, at least 5, or at least 10 additional generations, such as 2, 3, 4, 5, 6, 7, 8, 9, 10, 11, 12, 13, 14, 15, 16, 17, 18, 19 or 20 additional generations) with sufficient inbreeding to produce an inbred peanut plant derived from the new peanut variety 'Georgia-SP/RKN'. In other examples, the method includes (a) crossing a peanut plant derived from the new peanut variety 'Georgia-SP/RKN' with itself or another peanut plant to yield additional peanut variety 'Georgia-SP/RKN'-derived progeny peanut seed; (b) growing the progeny peanut seed of (a) under plant growth conditions, to yield additional peanut variety 'Georgia-SP/RKN'-derived peanut plants; and (c) repeating the crossing and growing steps of (a) and (b) from 0 to 7 times (such as 0 to 4 or 1 to 5 times, such as 0, 1, 2, 3, 4, 5, 6, or 7 times) to generate further peanut variety 'Georgia-SP/RKN'-derived peanut plants.

Methods are provided for developing a new peanut plant using the new 'Georgia-SP/RKN' variety. For example, the methods can include using 'Georgia-SP/RKN' plants or parts thereof as a source of breeding material in plant breeding techniques, such as recurrent selection, mass selection, bulk selection, backcrossing, pedigree breeding, genetic marker-assisted selection and genetic transformation. In some examples, a plant of the new peanut variety 'Georgia-SP/RKN' is used as the male or female parent.

The disclosure provides a first generation ($F_1$) hybrid peanut seed produced by crossing a plant of the new peanut variety 'Georgia-SP/RKN' to a second peanut plant. In some embodiments, the $F_1$ hybrid peanut plant is grown from the hybrid seed produced by crossing the new peanut variety 'Georgia-SP/RKN' to a second peanut plant.

Methods of producing hybrid peanut seeds are also provided. In one example the method includes crossing the new peanut variety 'Georgia-SP/RKN' to a second, distinct peanut plant which is non-isogenic to the new peanut variety 'Georgia-SP/RKN'. In some examples, the method includes cultivating peanut plants grown from seeds of the new peanut variety 'Georgia-SP/RKN' and cultivating peanut plants grown from seeds of a second, distinct peanut plant, until the plants bear flowers. A flower on one of the two plants is cross pollinated with the pollen of the other plant, and the seeds resulting from such a cross are harvested.

The disclosure also provides peanut plants and parts thereof produced by any of the methods disclosed herein. Thus, provided herein are plants of peanut variety 'Georgia-SP/RKN' that further include a single locus conversion, such as one or more desired traits, for example produced by backcrossing or genetic transformation. In some embodiments, the peanut plants produced by the disclosed methods includes at least two, at least three, at least four, at least five, or at least 10 of the traits of the new peanut variety 'Georgia-SP/RKN' as described herein, such as but not limited to RKN resistance, TSWV resistance, high oleic fatty acid concentration in seed oil, about 3% or less of TxAG-6 gene introgression on chromosome A09, high pod yield, overall disease resistance, large spanish market-type seed size with high percentage of Medium and Jumbo kernels (Table 7), medium-plus maturity, and good roasted nut flavor. In embodiments, at least 1 of the trats is RKN resistance. In some embodiments, the peanut plants produced by the disclosed methods include at least two, at least three, at least four, at least five, or at least 10 of the traits of the new peanut variety 'Georgia-SP/RKN' (see, e.g., Tables 1-11), such as 2, 3, 4, or all 5 of RKN resistance, TSWV resistance, high oleic fatty acid concentration in seed oil, about 3% or less of TxAG-6 gene introgression on chromosome A09, high pod yield, and the like.

Methods of producing a commodity plant product are provided. In some examples the method includes obtaining or supplying a plant of the new peanut variety 'Georgia-SP/RKN', or a part thereof, and producing the commodity plant product therefrom. In some examples the method includes growing and harvesting the plant, or a part thereof. Exemplary commodity plant products include but are not limited to a protein concentrate, a protein isolate, peanut oil, peanut butter, roasted peanuts, salted peanuts, livestock feed, peanut flour, soaps, and/or plastics.

The foregoing and other objects and features of the disclosure will become more apparent from the following detailed description.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1 illustrates a visual representation of GBS-based SNP genotyping results of chromosome (Chr.) A09 (chromosome shown in gray shading) for RKN-resistant cultivars 'Georgia-14N' and Georgia-SP/RKN compared to RKN-susceptible cultivar Georgia-06G with the TxAG-6 introgression shown as the dark gray/black portions/lines.

DETAILED DESCRIPTION

Description of Terms

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a plant" includes one or a plurality of such plants. The term "or" refers to a single element of stated alternative elements or a combination of two or more elements, unless the context clearly indicates otherwise. For example, the phrase "A or B" refers to A, B, or a combination of both A and B. Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. All references cited herein are incorporated by reference in their entireties.

In some examples, the numbers expressing quantities of ingredients, properties such as molecular weight, reaction conditions, and so forth, used to describe and claim certain embodiments are to be understood as being modified in some instances by the term "about" or "approximately." For example, "about" or "approximately" can indicate +/−20% variation of the value it describes. Accordingly, in some embodiments, the numerical parameters set forth herein are approximations that can vary depending upon the desired properties sought to be obtained by a particular embodiment. Notwithstanding that the numerical ranges and parameters setting forth the broad scope of some examples are approximations, the numerical values set forth in the specific examples are reported as precisely as practicable. The recitation of ranges of values herein is merely intended to serve as a shorthand method of referring individually to each separate value falling within the range.

Backcross: The mating of a hybrid to one of its parents. For example, hybrid progeny, for example a first-generation hybrid ($F_1$), can be crossed back one or more times to one of its parents. Backcrossing can be used to introduce one or more single locus conversions (such as one or more desirable traits) from one genetic background into another.

Cell. Cell as used herein includes a plant cell, whether isolated, in tissue culture or incorporated in a plant or plant part.

Cotyledon. A type of seed leaf. The cotyledon contains the food storage tissues of the seed.

Cross. Synonymous with hybridize or crossbreed. Includes the mating of genetically different individual plants, such as the mating of two parent plants.

Cross-pollination: Fertilization by the union of two gametes from different plants.

$F_1$ hybrid: The first-generation progeny of the cross of two non-isogenic plants.

Flower. Refers to all parts of the flower, including but not limited to, stigma, style, ovary, anther, filament, corolla, and calyx.

Gene. Refers to a segment of nucleic acid. As used herein a "gene" can refer to a hereditary unit corresponding to a sequence of DNA that occupies a specific location on a chromosome and that contains the genetic instruction for a characteristic(s) or trait(s) in an organism. The term gene can refer to translated and/or untranslated regions of a genome. "Gene" can refer to the specific sequence of DNA that is transcribed into an RNA transcript that can be translated into a polypeptide or be a catalytic RNA molecule, including but not limited to, tRNA, siRNA, piRNA, miRNA, long-non-coding RNA and shRNA. A gene can be introduced into a genome of a species, whether from a different species or from the same species, using transformation or various breeding techniques. In some examples, a gene encodes a desirable trait, such as disease, insect, or herbicide resistance.

Gene Silencing. A general term describing epigenetic processes of gene regulation, including any technique or mechanism in which the expression of a gene is prevented.

Genotype. The genetic constitution of a cell, an organism, or an individual (i.e., the specific allele makeup of the individual) usually with reference to a specific character under consideration.

High oleic fatty acid concentration. Oleic acid is a monounsaturated fatty acid found in plants such as peanuts, olives, sunflowers, and avocados that can contribute to healthy cholesterol and has high oxidative stability, contributing to longer shelf-life of manufactured products. Peanuts with high oleic to linoleic fatty acid ratio produce seed oil with a greater concentration of oleic fatty acid than conventional peanuts, contributing to longer shelf-life and healthier oil qualities. In embodiments, high oleic peanuts have an oleic:linoleic ratio of about 35:1-40:1, as compared to normal oleic/conventional peanuts which have an oleic:linoleic ratio of about 1:1 to 4:1.

Leaf scorch/pepper spot disease: "Leaf scorch" and "pepper spot" describe two different disease symptoms, sometimes occurring alone, sometimes together, but both are caused by the fungus *Leptosphaerulina crassiasca* (Sechet) Jackson and Bell. Often the disease is referred to as "leaf scorch", "pepper spot", or "leaf scorch/pepper spot". It is primarily a cosmetic issue in typical commercial production fields; however, the disease can be lethal in research greenhouses.

Maturity date: The evaluation of plants considered as mature when the highest percentage of the pods have reached the mature colors, black, brown, and orange.

Peanut flour. Flour high in protein, often used as a gluten-free solution. Can be generated from peanuts obtained from the disclosed new variety.

Peanut oil. Often used in cooking, it has a mild flavor, high smoke point, and high monounsaturated content. Variations include aromatic roasted peanut oil, refined peanut oil, extra virgin or cold pressed peanut oil, and peanut extract. Can be generated from peanuts obtained from the disclosed new variety.

Plant: Includes reference to an immature or mature whole plant, including a plant from which seed, roots or leaves have been removed. Seed or embryo that will produce the plant is also considered to be the plant.

Plant height. Plant height is taken from the top of the soil to the tip of the plant main stem, and is typically measured in centimeters or inches.

Plant parts. Includes protoplasts, leaves, stems, roots, root tips, anthers, pistils, seed, embryo, pollen, ovules, cotyledon, hypocotyl, flower, shoot, tissue, petiole, cells, pods, meristematic cells and the like. Includes plant cells of a tissue culture from which peanut plants can be regenerated.

Pod. Refers to the fruit of a peanut plant. It includes the hull or shell (pericarp) and the peanut seeds.

Progeny. Offspring; descendants. Includes an $F_1$ peanut plant produced from the cross of two peanut plants where at least one plant includes peanut cultivar 'Georgia-SP/RKN', and progeny further includes, but is not limited to, subsequent $F_2$, $F_3$ $F_4$, $F_5$, $F_6$, $F_7$, $F_3$, $F_9$, and $F_{10}$ generational crosses with the recurrent parental line.

Regeneration. The development of a plant from tissue culture. The cells may or may not have been genetically modified. Plant tissue culture relies on the fact that all plant cells have the ability to generate a whole plant (totipotency). Single cells (protoplasts), pieces of leaves, or roots can often be used to generate a new plant on culture media given the required nutrients and plant hormones.

Relative maturity: Refers to the maturity grouping designated by the peanut industry over a given growing area. This figure is generally divided into tenths of a relative maturity group. Within narrow comparisons, the difference of a tenth of a relative maturity group equates very roughly to a day difference in maturity at harvest.

Resistance. The ability of a plant to prevent and/or have lower incidence of infection from disease and/or pests, such as, but not limited to RKN, TSWV than similar cultivars.

Root-knot nematode (RKN). Refers to organisms from the genus *Meloidogyne* that are plant-parasitic nematodes that infect plants worldwide and cause significant crop damage. *Meloidogyne arenaria* (Neal) are a species of RKN especially problematic for peanut crops.

Seed. The part of a flowering plant that typically contains the embryo with its protective coat and stored food and that can develop into a new plant under the proper conditions. Seed can refer to a fertilized and mature ovule.

Self-pollination: The transfer of pollen from the anther to the stigma of the same plant.

Single locus converted (conversion) plant: Plants developed by backcrossing and/or by genetic transformation, where essentially all of the desired morphological and physiological characteristics of a peanut variety are recovered in addition to the characteristics of the single locus transferred into the variety via the backcrossing technique.

Tissue culture: A composition that includes isolated cells of the same or a different type or a collection of such cells organized into parts of a plant.

Tomato Spotted Wilt Virus (TSWV). A spherical negative-sense RNA virus within the family Bunyaviridae. TSV, which is commonly transmitted by thrips, causes serious losses in economically important crops and it is one of the most economically devastating plant viruses in the world.

Transformation. The introduction of new genetic material (e.g., exogenous transgenes) into plant cells. Exemplary mechanisms that are to transfer DNA into plant cells include (but not limited to) electroporation, microprojectile bombardment, *Agrobacterium*-mediated transformation and direct DNA uptake by protoplasts.

Transgene. A gene or genetic material that has been transferred into the genome of a plant, for example by genetic engineering methods. Exemplary transgenes include a cDNA (complementary DNA) segment, which is a copy of mRNA (messenger RNA), and the gene itself residing in its original region of genomic DNA. For instance, a transgene can refer to a segment of DNA containing a gene sequence that is introduced into the genome of a peanut plant or plant cell. This non-native segment of DNA may retain the ability to produce RNA or protein in the transgenic plant, or it may alter the normal function of the transgenic plant's genetic code. In general, the transferred nucleic acid is incorporated into the plant's germ line. Transgene can also describe any DNA sequence, regardless of whether it contains a gene coding sequence or it has been artificially constructed, which has been introduced into a plant or vector construct in which it was previously not found.

DISCUSSION

New High Oleic Peanut Resistant to Root-Knot Nematode (RKN)

The present disclosure relates to a new peanut variety, 'Georgia-SP/RKN'. This new variety has high oleic fatty acid concentration, is highly RKN resistant and TSWV resistant and high yielding. In some examples, 'Georgia-SP/RKN' also has various characteristics such as, but not limited to overall high disease resistance, high pod yield, small percentage of large fancy pods (e.g., 13.49 mm size distribution), high percentage of total meat content, medium-plus maturity, runner growth habit, large seed size, tan seedcoat (testa) color, or combinations thereof. Thus, the new variety is adapted to growth in the United States that commonly grow peanut cultivars and to areas that are known to have or expected to have RKN and/or TSWV.

In some examples, a 'Georgia-SP/RKN' plant or progeny thereof had a mid-season TSWV susceptibility of 1.8 to 4.2% over 4 trials grown in 2 years; late season total disease count ranged from 1.2 to 6.8% over 4 trials grown in 2 years. Susceptibility to TSWV and late season total disease was significantly lower than most spanish market-type cultivars tested (Table 3 & 4).

On the other hand, leaf scorch or pepper spot disease symptoms caused by the fungus *Leptosphaerulina crassiasca* (Sechet) Jackson and Bell, is primarily a cosmetic issue. Leaf scorch symptom ratings were higher in Georgia-SP/RKN (6.6) compared to Georgia-17SP (4.4), a closely related line, and could potentially be used as a diagnostic for identification.

Root-knot nematode resistance, as measured by RKN count (number of J2 stage root-knot nematodes in 100 $cm^3$ soil; lower number indicates higher resistance), ranged from 0 to 57, whereas susceptible check cultivars ranged from 93 to 867 RKN count in 2 trials grown in 2019 (Table 10). Visual gall ratings, a percentage of obviously infected tissue for roots and pods, indicated root galling of 0 to 0.3% for Georgia-SP/RKN, lower than the comparison cultivars, which ranged from 6.5 to 53.3% (Table 10). Pod galling in Georgia-SP/RKN was also reduced with pod galling of 0% compared to the susceptible cultivars with 10.5 and 60.0%.

Thus, provided herein is a seed of peanut variety 'Georgia-SP/RKN', wherein representative sample seed of the variety is deposited under ATCC Accession No. PTA-127584 (NPGS PI No. PI #700991). Also provided are bulk peanut seed containing such seeds. The disclosure provides peanut plants having or consisting of the morphological and physiological characteristics of 'Georgia-SP/RKN'. The disclosure also provides peanut plants having one or more of (such as at least two, at least three, at least four, at least five, at least 6, at least 7, at least 8, at least 9, or at least 10 of) the morphological and physiological characteristics of 'Georgia-SP/RKN' (such as those listed in Examples 2-11 and/or Tables 2-11). In embodiments, at least one of the characteristics is RKN resistance. Also provided are seeds of such plants, progeny of such plants, parts of such plants (such as pollen, ovules and cells). In one example, the disclosure provides peanut plants having the genotype of 'Georgia-SP/RKN'. For example, the disclosure provides plants produced by growing the seed of the new peanut variety 'Georgia-SP/RKN'.

The disclosed 'Georgia-SP/RKN' plants, and in some examples progeny thereof, are a high-yielding, high-oleic, large-seeded spanish market type peanut cultivar with intermediate decumbent runner growth habit, tan testa color, medium plus maturity, high TSWV resistance, and a high level of RKN resistance, where the level of RKN resistance is higher than peanut cultivar 'Georgia-17SP'.

The disclosed 'Georgia-SP/RKN' plants and seeds can be used to produce other peanut plants and seeds, for example as part of a breeding program. Choice of breeding or selection methods using to generate new peanut plants and seeds can depend on the mode of plant reproduction, the heritability of the trait(s) being improved, and the type of variety used commercially (e.g., $F_1$ hybrid variety, pure line variety, etc.). For highly heritable traits, a choice of superior individual plants evaluated at a single location can be effective, whereas for traits with low heritability, selection can be based on mean values obtained from replicated evaluations of families of related plants. Popular selection methods commonly include pedigree selection, modified pedigree selection, mass selection, recurrent selection and backcrossing.

The complexity of inheritance influences choice of the breeding method. Backcross breeding can be used to transfer one or a few favorable genes for a highly heritable trait into a desirable variety. This approach has been used for breeding disease-resistant varieties (e.g., see Bowers et al., 1992. *Crop Sci.* 32(1):67-72; Nickell and Bernard, 1992. *Crop Sci.* 32(3):835). Various recurrent selection techniques can be used to improve quantitatively inherited traits controlled by numerous genes.

Promising advanced breeding lines can be thoroughly tested and compared to appropriate standards in environments representative of the commercial target area(s) for generally three or more years. The best or most preferred lines are candidates for new commercial varieties. Those still deficient in a few traits may be used as parents to produce new populations for further selection.

One method of identifying a superior plant is to observe its performance relative to other experimental plants and to one or more widely grown standard varieties. Single observations can be generally inconclusive, while replicated observations provide a better estimate of genetic worth.

Plant breeding can result in new, unique and superior peanut varieties and hybrids from 'Georgia-SP/RKN'. Two or more parental lines can be selected (such as 'Georgia-SP/RKN' as one of the lines), followed by repeated selfing and selection, producing many new genetic combinations. Each year, the germplasm to advance to the next generation is selected. This germplasm is grown under unique and different geographical, climatic and soil conditions, and further selections are then made, during and at the end of the growing season.

In some examples, new peanut varieties developed from 'Georgia-SP/RKN' (such as $F_1$, $F_2$, $F_3$, $F_4$, $F_5$, $F_6$, $F_7$ $F_3$, $F_9$, or $F_{10}$ progeny, or even later progeny) are exposed to TSWV and/or *Leptosphaerulina crassiasca* (Séchet) Jackson and Bell to confirm they are resistant or susceptible to such diseases.

The development of new peanut varieties from 'Georgia-SP/RKN' involves the development and selection of peanut varieties, the crossing of these varieties and selection of progeny from the superior hybrid crosses. A hybrid seed is produced by manual crosses between selected male-fertile parents or by using male sterility systems. Hybrids can be identified by using certain single locus traits such as pod color, flower color, seed color, or pubescence color, which indicate that the seed is truly a hybrid. Additional data on parental lines as well as the phenotype of the hybrid can influence a decision whether to continue with the specific hybrid cross.

Pedigree breeding and recurrent selection breeding methods can be used to develop varieties from breeding populations. Breeding programs combine desirable traits from two or more varieties or various broad-based sources into breeding pools from which varieties are developed by selfing and selection of desired phenotypes. Pedigree breeding is commonly used for the improvement of self-pollinating crops. Two parents (e.g., wherein one of the parents is 'Georgia-SP/RKN') which possess favorable, complementary traits are crossed to produce an $F_1$. An $F_2$ population is produced by allowing one or several $F_1$ peanut plants to self-pollinate. Selection of the best or most preferred individuals usually begins in the $F_2$ population (or later depending upon the breeding objectives); then, beginning in the $F_3$, the best or most preferred individuals in the best families can be selected. Replicated testing of families can begin in the $F_3$ or $F_4$ generation to improve the effectiveness of selection for traits with low heritability. At an advanced stage of inbreeding (e.g., $F_6$ and $F_7$), the best lines or mixtures of phenotypically similar lines can begin replicated testing for potential commercial release as new varieties.

Mass and recurrent selections can be used to improve populations of either self- or cross-pollinating crops. A genetically variable population of heterozygous individuals is either identified or created by intercrossing several different parents. The best or most preferred plants are selected based on individual superiority, outstanding progeny, or excellent combining ability. The selected plants are intercrossed to produce a new population in which further cycles of selection are continued.

Backcross breeding can be used to transfer genetic loci for simply inherited, highly heritable traits into a desirable homozygous variety which is the recurrent parent (e.g., 'Georgia-SP/RKN'). The source of the trait to be transferred is called the donor or nonrecurrent parent. The resulting plant is expected to have the attributes of the recurrent parent (e.g., variety) and the desirable trait transferred from the donor parent. After the initial cross, individuals possessing the phenotype of the donor parent are selected and repeatedly crossed (backcrossed) to the recurrent parent. The resulting plant is typically expected to have the attributes of the recurrent parent (e.g., variety) and the desirable trait transferred from the donor parent.

The single-seed descent procedure can refer to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population are represented by a progeny when generation advance is completed.

In a multiple-seed procedure, one or more pods from each plant in a population are commonly harvested and threshed together to form a bulk. Part of the bulk is used to plant the next generation and part is put in reserve. The procedure has been referred to as modified single-seed descent or the pod-bulk technique. The multiple-seed procedure has been used to save labor at harvest. It is faster to thresh pods with a machine than to remove one seed from each by hand for the single-seed procedure. The multiple-seed procedure also makes it possible to plant the same number of seeds of a population each generation of inbreeding. Sufficient numbers of seeds are harvested to make up for those plants that did not germinate or produce seed.

Descriptions of other breeding methods commonly used for different traits and crops can be found in one of several reference books (e.g., Allard. 1960. Principles of plant breeding. Davis, California: John Wiley & Sons, NY, University of California, pp. 50-98; Simmonds. 1979. Principles of crop improvement. New York: Longman, Inc., pp. 369-399; Sneep and Hendriksen. 1979. "Plant breeding perspectives." Wageningen (ed.), Center for Agricultural Publishing and Documentation; Fehr. 1987. "Principles of variety development." Theory and Technique (Vol. 1). Methods for transformation and regeneration of peanut cells, and specific genes associated with improved peanut traits that may be introduced into 'Georgia-SP/RKN' include those described in Ozias-Akins et al., Plant Science 93:185-194 (1993). In addition, methods for producing novel peanut lines through selection are described in Moore et al., J. Heredity 80(3): 252 (1989); Norden, A. J., Peanuts, Culture and Uses. Am. Peanut Res. And Educ. Soc., Stillwater, Okla. (C. T. Wilson ed. 1973); Norden, A. J. in Hybridization of Crop Plants (H. H. Hadley ed. 1980); Norden et al., Breeding of the cultivated peanut in Peanut Science and Technology, (H. E. Pattee ed. 1992); Norden et al., Florida Agr. Res. 3:16-18 (1984); Knauft et al., Peanut, Peanut Principles of Cultivar Development, 2:346-384 (Walter R. Fehr ed. 1987).

Breeding Peanut Variety 'Georgia-SP/RKN'

Methods for crossing the new peanut variety 'Georgia-SP/RKN' with itself or a second plant are provided, as are the seeds and plants produced by such methods. Such methods can be used for propagation of the new peanut variety 'Georgia-SP/RKN', or progeny thereof, can be used to produce hybrid peanut seeds and the plants grown therefrom. Hybrid peanut plants can be used, for example, in the commercial production of peanut products or in breeding programs for the production of novel peanut varieties. A hybrid plant can also be used as a recurrent parent at any given stage in a backcrossing protocol during the production of a single locus conversion (for example introduction of one or more desirable traits) of the new peanut variety 'Georgia-SP/RKN'.

Methods of producing peanut plants and/or seed are provided. Such a method can include crossing the new peanut variety 'Georgia-SP/RKN' with itself or a second peanut plant and harvesting a resulting peanut seed, such as an $F_1$ hybrid seed. The resulting plant can be grown, resulting in a peanut plant or part thereof.

In one example methods of producing an inbred peanut plant derived from peanut variety 'Georgia-SP/RKN' are provided. In one example such methods include (a) preparing a progeny plant derived from peanut variety 'Georgia-SP/RKN' by crossing a plant of the peanut variety 'Georgia-SP/RKN' with a peanut plant of a second variety; (b) crossing the progeny plant with itself or a second plant to produce a seed of a progeny plant of a subsequent generation; (c) growing a progeny plant of a subsequent generation from said seed and crossing the progeny plant of a subsequent generation with itself or a second plant; and (d) repeating steps (b) and (c) for an additional at least 2 generations (such as at least 3, at least 4, at least 5, at least 6, at least 7, at least 8 at least 9, at least 10, at least 15 or at least 20, such as 2 to 10, 3 to 10, or 3 to 15 generations) with sufficient inbreeding to produce an inbred peanut plant derived from the peanut variety 'Georgia-SP/RKN'.

The second plant crossed with the new peanut variety 'Georgia-SP/RKN' for the purpose of developing novel peanut varieties, is typically a plant which either themselves exhibit one or more desirable characteristics or which exhibit one or more desired characteristic(s) when in hybrid combination. In one example, the second peanut plant is transgenic. Exemplary desired characteristics include, but are not limited to, one or more of: increased seed yield, lodging resistance, emergence, increased seedling vigor, modified maturity date, desired plant height, high oil content, high protein content, herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination; abiotic stress tolerance; modified phosphorus content, modified antioxidant content; modified essential seed amino acid content, modified fatty acid content, modified carbohydrate content, modified peanut fiber content, low pod-splitting, modified seed yield, modified oil percent, modified protein percent, modified fancy pod percent, modified pod size, modified pod shape, and modified pod color.

When the new peanut variety 'Georgia-SP/RKN' is crossed with another different variety, first generation ($F_1$) peanut progeny are produced. The hybrid progeny are produced regardless of characteristics of the two varieties produced. As such, an $F_1$ hybrid peanut plant can be produced by crossing 'Georgia-SP/RKN' with any second peanut plant. The second peanut plant can be genetically homogeneous (e.g., inbred) or can itself be a hybrid. Therefore, the disclosure provides any $F_1$ hybrid peanut plant produced by crossing the new peanut variety 'Georgia-SP/RKN' with a second peanut plant (such as a transgenic plant having one or more genes that confer to the plant one or more desired characteristics).

Although currently peanut production in the US is strictly non-GMO and thus modification of peanut plants by the addition of transgenes is unlikely; it is appreciated that such modifications could be desirable in the future and such modification is understood by those of skill in the art and contemplated to fall within the scope of the present disclosure.

Peanut plants can be crossed by either natural or mechanical techniques. Natural pollination occurs in peanut plants either by self-pollination or natural cross pollination, which typically is aided by pollinating organisms. In either natural or artificial crosses, flowering time can be a consideration.

The peanut plant grows best in light, sandy soil and typically requires four to five months of warm weather and an annual rainfall of 20 to 39 inches, or the equivalent in irrigation water. The pea-like yellow flowers form in axillary clusters and only bloom for a short time. Following self-pollination, the stalk at the base of the ovary, called the pedicel, elongates rapidly and turns downward to bury the fruits one to several inches below the ground surface. The peanut pods complete their development 120 to 150 days after planting. During harvest, the entire plant including the roots is removed from the soil.

In some examples, the crossing of two peanut plants is accomplished using artificial hybridization. In artificial hybridization, the flower used as a female in a cross is manually cross pollinated prior to maturation of pollen from the flower, thereby preventing self-fertilization, or alternatively, the male parts of the flower are emasculated. Exemplary methods for emasculating the male parts of a peanut flower include physical removal of the male parts, use of a cytoplasmic or genetic factor conferring male sterility, and application of a chemical gametocide to the male parts.

For artificial hybridization employing emasculation, flowers that are expected to open the following day are selected on the female parent. The flower buds emerge from the leaf axils sufficiently for manipulation in the afternoon. Usually no more than one bud is prepared at each inflorescence on a parent plant. The calyx is either folded down or removed entirely, for example by grasping a sepal with the forceps and pulling it down and around the flower. The exposed standard petals are folded back and held with thumb and fore-finger. The wing petals are then moved down or removed entirely and the keel is removed to expose the stigma, filaments, and anthers. All of the anthers are removed and most of the filaments to prevent accidental self-pollination. The standard petals are then placed back to protect the stigma overnight and the flower is tagged using various methods to identify fresh emasculations.

The following morning, any non-emasculated, self-pollinated flowers present on target plants are removed to prevent self-pollinated peanut seed development. Tagged, emasculated flowers are pollinated early in the morning using pollen from designated parental plants. Pollen is extracted from healthy flowers on the parent plant using forceps and the pollen is then gently placed on the stigma of the emasculated flower. Pollen shed typically begins in the morning between 0700-1000, though pollen shed can also begin later and continue throughout much of the day with more moderate temperatures. Desiccators containing calcium chloride crystals are used in some environments to dry male flowers to obtain adequate pollen shed or preserve fresh pollen for several days. Hybrid pegs resulting from successful cross-fertilization, usually extend from the leaf axil 5-10 days after pollination. The hybrid peg is then marked with a colored wire or tag and the hybrid seed harvested approximately 2 months later.

Peanut Plants Having One or More Desired Heritable Traits

The disclosure provides plants of the new peanut variety 'Georgia-SP/RKN' modified to include one or more desired heritable traits. In some examples, such plants can be developed using backcrossing or genetic engineering (for example by introducing one or more transgenes into the 'Georgia-SP/RKN' variety, wherein the transgenes encode one or more desired traits), wherein essentially all of the desired morphological and physiological characteristics of the 'Georgia-SP/RKN' variety are recovered, such as RKN resistance (in some embodiments with about 3% or less of the TxAG-6 introgression in chromosome A09), and in some examples one or more of high oleic fatty acid concentration in seed oil, TSWV resistance, high percentage of total sound mature kernels (TSMK), high pod yield, small percentage of large fancy pods (e.g., 13.49 mm size distribution), high percentage of total meat content, large spanish-type seed size distribution, large percentage of Medium and Jumbo seeds (seeds riding a 7.14 mm by 19.05 mm screen and a 8.33 mm by 19.05 mm screen, respectively), medium plus maturity, runner growth habit, dark green foliage, and tan seedcoat (testa) color, or combinations thereof, in addition to a genetic locus transferred into the plant via the backcrossing technique. Plants developed using such methods can be referred to as a single locus converted plant.

In one example, the method of introducing one or more desired traits into peanut variety 'Georgia-SP/RKN' includes (a) crossing a plant of variety 'Georgia-SP/RKN' with a second plant having one or more desired traits to produce $F_1$ progeny plants; (b) selecting $F_1$ progeny plants that have the one or more desired traits to produce selected $F_1$ progeny plants; (c) crossing the selected progeny plants with at least a first plant of variety 'Georgia-SP/RKN' to produce backcross progeny plants; (d) selecting backcross progeny plants that have the one or more desired traits and physiological and morphological characteristics of peanut variety 'Georgia-SP/RKN' to produce selected backcross progeny plants; and (e) repeating steps (c) and (d) one or more times in succession to produce selected second or higher backcross progeny plants that have the one or more desired traits and the physiological and morphological characteristics of peanut variety 'Georgia-SP/RKN' when grown in the same environmental conditions.

Backcrossing methods can be used to improve or introduce a characteristic into the new peanut variety 'Georgia-SP/RKN' (for example using the methods provided in U.S. Pat. No. 6,140,556). The parental peanut plant which contributes the locus for the desired characteristic is termed the "nonrecurrent" or "donor" parent. This terminology refers to the fact that the nonrecurrent parent is used one time in the backcross protocol and therefore does not recur. The parental peanut plant to which the locus or loci from the nonrecurrent parent are transferred is known as the recurrent parent as it is used for several rounds in the backcrossing protocol (Poehlman and Sleper. 1995. "Breeding Field Crops" Ames, Iowa: Iowa State University Press; Fehr. 1987. "Principles of variety development." In Theory and Technique (Vol. 1) and Crop Species peanut (Vol. 2). New York: Macmillan Publishing Company, pp. 360-376; Sprague and Dudley, eds. 1988. Corn and Improvement, 3rd edition). In a typical backcross protocol, the original variety of interest (recurrent parent, e.g., 'Georgia-SP/RKN') is crossed to a second variety (nonrecurrent parent) that carries the single locus of interest (such as a desirable trait) to be transferred. The resulting progeny from this cross are then crossed again to the recurrent parent and the process is repeated until a peanut plant is obtained wherein essentially all of the desired morphological and physiological characteristics of the recurrent parent (e.g., 'Georgia-SP/RKN') are recovered (such as RKN resistance, and in some examples one or more of high oleic fatty acid concentration in seed oil, TSWV resistance, high percentage of total sound mature kernels (TSMK), high pod yield, small percentage of large fancy pods (e.g., 13.49 mm size distribution), high percentage of total meat content, large seed size distribution, large percentage of jumbo seeds, medium plus maturity, runner growth habit, medium-large runner seed size, and tan seedcoat (testa) color, or combination thereof) in the converted plant, in addition to the single transferred locus from the nonrecurrent parent.

The goal of a backcross protocol is to alter or substitute a single trait or characteristic in the original variety, such as 'Georgia-SP/RKN'. To accomplish this, a single locus of the recurrent variety is modified or substituted with the desired locus from the donor, or nonrecurrent parent, while retaining essentially all of the rest of the desired genetic traits, and therefore the desired physiological and morphological constitution of the original, recurrent parental variety. The choice of the particular donor parent can depend on the purpose of the backcross; for example, a major purpose is to add a commercially desirable, agronomically important trait to the plant. The exact backcrossing protocol can depend on the characteristic or trait being altered to determine an appropriate testing protocol. Although backcrossing methods are simplified when the characteristic being transferred is a dominant allele, a recessive allele can also be transferred. In this instance, it can be useful to introduce a test of the progeny to determine if the desired characteristic has been successfully transferred.

In a backcross where the desired characteristic being transferred to the recurrent parent is controlled by a major gene which can be readily evaluated during the backcrossing, it is common to conduct enough backcrosses to avoid testing individual progeny for specific traits such as yield in extensive replicated tests. In general, four or more backcrosses are used when there is no evaluation of the progeny for specific traits, such as yield or resistance to a pest. As in this example, lines with the phenotype of the recurrent parent can be composited without the usual replicated tests for traits such as yield, protein or oil percentage in the individual lines.

Peanut varieties can also be developed from more than two parents, for example using modified backcrossing, which uses different recurrent parents during the backcrossing. Modified backcrossing can be used to replace the original recurrent parent with a variety having certain more desirable characteristics, or multiple parents can be used to obtain different desirable characteristics from each.

Many single locus traits are known that are not regularly selected for in the development of a new inbred but that can be improved by backcrossing techniques. Single locus traits can be, but are not necessarily, transgenic. Examples of these traits include, but are not limited to, male sterility, herbicide resistance, abiotic stress tolerance (such as tolerance or resistance to drought, heat, cold, low or high soil pH level, and/or salt), resistance to bacterial, fungal, or viral disease, insect resistance, restoration of male fertility, enhanced nutritional quality, modified phosphorus content, modified antioxidant content; modified essential seed amino acid content, modified fatty acid content, modified carbohydrate content, modified peanut fiber content, yield stability, and yield enhancement, low pod-splitting, modified seed yield, modified oil percent, modified protein percent, modified fancy pod percent, modified pod size, modified pod shape, and modified pod color. These comprise genes generally inherited through the nucleus. Thus, plants of peanut variety 'Georgia-SP/RKN' that include a single locus conversion (such as one that confers a desired trait) are provided herein.

Selection of peanut plants for breeding may not be dependent on the phenotype of a plant and instead can be based on genetic investigations. For example, a suitable genetic marker can be used which is closely genetically linked to a desired trait. One of these markers can therefore be used to identify the presence or absence of a trait in the offspring of a particular cross, and hence can be used in selection of progeny for continued breeding. This technique is referred to as marker assisted selection. Any other type of genetic marker or other assay which is able to identify the relative presence or absence of a trait of interest in a plant can also be useful for breeding. Procedures for marker assisted selection applicable to the breeding of peanut are known. Such methods can be useful in the case of recessive traits and variable phenotypes, or where conventional assays are more expensive, time consuming or otherwise disadvantageous. Types of genetic markers which can be used, but are not limited to, Simple Sequence Repeat polymorphisms (SSRs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858), and Single Nucleotide Polymorphisms (SNPs).

Qualitative characters can be useful as phenotype-based genetic markers in peanuts; however, some or many may not differ among varieties commonly used as parents. Widely used genetic markers include flower color, seed color, and pod color. Differences in maturity, height, TSMK percentage, fancy pod percentage, seed size, seed weight, and pest resistance between parents can also be used to verify hybrid plants.

Useful or desirable traits can be introduced by backcrossing, as well as directly into a plant by genetic transformation methods. Genetic transformation can therefore be used to insert a selected transgene into the 'Georgia-SP/RKN' variety or can, alternatively, be used for the preparation of transgenes which can be introduced by backcrossing. Thus, the disclosure provides methods of producing a plant of peanut variety 'Georgia-SP/RKN' that includes one or more added desired traits, for example that include introducing a transgene(s) conferring the one or more desired traits into a plant of peanut variety 'Georgia-SP/RKN' (for example by transformation with a transgene that confers upon the peanut plant the desired trait), thereby producing a plant of peanut variety 'Georgia-SP/RKN' that includes the one or more added desired traits.

Methods for the transformation of many economically important plants, including peanuts, are known. Methods for introducing a desired nucleic acid molecule (e.g., transgene), such as DNA, RNA, or inhibitory RNAs, are known, and the disclosure is not limited to particular methods. Exemplary techniques which can be employed for the genetic transformation of peanut include, but are not limited to, electroporation, microprojectile bombardment, *Agrobacterium*-mediated transformation direct DNA uptake by protoplasts, sonication of target cells, liposome and spheroplast fusion, CaCl2 precipitation, polyvinyl alcohol, or poly-L-ornithine.

To effect transformation by electroporation, friable tissues, such as a suspension culture of cells or embryogenic callus, can be used. Alternatively, immature embryos or other organized tissue can be transformed directly. In this technique, the cell walls of target cells can be partially degraded by exposing them to pectin-degrading enzymes (pectolyases) or mechanically wound tissues in a controlled manner.

Protoplasts can also be employed for electroporation transformation of plants (Bates. 1994. *Mol. Biotechnol.* 2(2):135-145; Lazzeri. 1995. *Methods Mol. Biol.* 49:95-106). For example, the generation of transgenic peanut plants by electroporation of cotyledon-derived protoplasts and whole cells and tissues has been described (Donn et al., In Abstracts of VIIth International Congress on Plant Cell and Tissue Culture IAPTC, A2-38, p. 53 (1990); D'Halluin et al., Plant Cell, 4:1495-1505 (1992); and Spencer et al., Plant Mol. Biol., 24:51-61 (1994)).

In microprojectile bombardment, particles (such as those comprised of tungsten, platinum, or gold) are coated with nucleic acids and delivered into cells by a propelling force. For the bombardment, cells in suspension are concentrated on filters or solid culture medium. Alternatively, immature embryos or other target cells can be arranged on solid culture medium. The cells to be bombarded are positioned at an appropriate distance below the macroprojectile stopping plate. An exemplary method for delivering DNA into plant cells by acceleration is the Biolistics Particle Delivery System, which can be used to propel particles coated with DNA or cells through a screen, such as a stainless steel or Nytex screen, onto a surface covered with target peanut cells. The screen disperses the particles so that they are not delivered to the recipient cells in large aggregates. A screen intervening between the projectile apparatus and the cells to be bombarded can reduce the size of projectiles aggregate and contribute to a higher frequency of transformation by reducing the damage inflicted on the recipient cells by projectiles that are too large. Microprojectile bombardment methods can be used to transform peanuts, as described, for example, in U.S. Pat. No. 5,322,783.

*Agrobacterium*-mediated transfer can be used to introduce gene loci into plant cells. DNA can be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations (Klee et al. 1985. *Bio. Tech.* 3(7):637-342). Moreover, vectors for *Agrobacterium*-mediated gene transfer have improved the arrangement of genes and restriction sites in the vectors to facilitate the construction of vectors capable of expressing various polypeptide coding genes. Such vectors have convenient multi-linker regions flanked by a promoter and a polyadenylation site for direct expression of inserted polypeptide coding genes. Additionally, *Agrobacterium* containing both armed and disarmed Ti genes can be used for transformation. The use of *Agrobacterium*-mediated plant integrating vectors to introduce DNA into plant cells is known (e.g., Fraley et al. 1985. *Bio. Tech.* 3(7):629-635; U.S. Pat. No. 5,563,055), and its use for peanut transformation has been described (Chee and Slightom. 1995. *Methods Mol. Biol.* 44:101-119; U.S. Pat. No. 5,569,834). Briefly, plant tissue (often leaves) is cut into small pieces, e.g. 10 mm×10 mm, and soaked for 10 minutes in a fluid containing suspended *Agrobacterium*. Some cells along the cut will be transformed by the bacterium, which inserts its DNA into the cell, which is placed on selectable rooting and shooting media, allowing the plants to regrow. Some plants can be transformed just by dipping the flowers into suspension of *Agrobacterium* and then planting the seeds in a selective medium.

Transformation of plant protoplasts can also be achieved using methods based on calcium phosphate precipitation, polyethylene glycol treatment, electroporation, and combinations of these treatments (e.g., Potrykus et al. 1985. *Mol. Gen. Genet.* 199(2):169-177; Omirulleh et al. 1993. *Plant Mol. Biol.* 21(3):415-428; Fromm et al. 1986. *Nature*. 319 (6056):791-739; Uchimiya et al. 1986. *Mol. Gen. Genet.* 204(2):207-207; Marcotte et al. 1988. *Nature* 335(6189):

454-457). The ability to regenerate peanut plants from protoplasts makes these techniques applicable to peanut.

In one example, such methods can also be used to introduce transgenes for the production of proteins in transgenic peanuts. The resulting produced protein can be harvested from the transgenic peanut. The transgene can be harvested from the transgenic plants that are originated or are descended from the new peanut variety 'Georgia-SP/RKN', a seed of 'Georgia-SP/RKN' or a hybrid progeny of 'Georgia-SP/RKN'.

Numerous different genes are known and can be introduced into a peanut plant 'Georgia-SP/RKN' or progeny thereof. Non-limiting examples of particular genes and corresponding phenotypes that can be chosen for introduction into a peanut plant are provided herein.

Herbicide Resistance

Numerous herbicide resistance genes are known and can be used with the methods and plants provided herein. In particular examples, a herbicide resistance gene confers tolerance to an herbicide comprising glyphosate, sulfonylurea, imidazalinone, dicamba, glufosinate, phenoxy proprionic acid, cyclohexone, triazine, benzonitrile, broxynil, L-phosphinothricin, cyclohexanedione, chlorophenoxy acetic acid, or combinations thereof.

In one example the herbicide resistance gene is a gene that confers resistance to an herbicide that inhibits the growing point or meristem, such as an imidazalinone or a sulfonylurea. Exemplary genes in this category code for mutant ALS and AHAS enzyme as described, for example, by Lee et al. (1988. *Embryo J.* 7:1241-8) and Miki et al. (1990. *Theoret. Appl. Genet.* 80:449-458).

Resistance genes for glyphosate (e.g., resistance conferred by mutant 5-enolpyruvl-3 phosphikimate synthase (EPSP) and aroA genes, respectively) and other phosphono compounds such as glufosinate (phosphinothricin acetyl transferase (PAT) and *Streptomyces hygroscopicus* phosphinothricin-acetyl transferase (bar) genes), pyridinoxy or phenoxy proprionic acids, and cyclohexanediones (ACCase inhibitor-encoding genes), can be used (e.g., see U.S. Pat. Nos. 4,940,835; 5,627,061; 6,566,587, 6,338,961, 6,248,876, 6,040,497, 5,804,425, 5,633,435, 5,145,783, 4,971,908, 5,312,910, 5,188,642, 4,940,835, 5,866,775, 6,225,114, 6,130,366, 5,310,667, 4,535,060, 4,769,061, 5,633,448, 5,510,471, RE 36,449, RE 37,287, 5,491,288, 5,776,760, 5,463,175, 7,462,481; and International Publications EP1173580, WO 01/66704, EP1173581, and EP1173582). Examples of specific EPSPS transformation events conferring glyphosate resistance are described, for example, in U.S. Pat. No. 6,040,497.

DNA molecules encoding a mutant aroA gene are known (e.g., ATCC accession number 39256 and U.S. Pat. No. 4,769,061), as are sequences for glutamine synthetase genes, which confer resistance to herbicides such as L-phosphinothricin (e.g., U.S. Pat. No. 4,975,374), phosphinothricin-acetyltransferase (e.g., U.S. Pat. No. 5,879,903). DeGreef et al. (1989. *Bio/Technology* 61-64) describe the production of transgenic plants that express chimeric bar genes coding for phosphinothricin acetyl transferase activity. Exemplary genes conferring resistance to phenoxy propionic acids and cyclohexones, such as sethoxydim and haloxyfop are the Acct-S1, Accl-S2 and Acct-S3 genes described by Marshall et al. (1992. *Theor Appl Genet.* 83:435-442).

Genes conferring resistance to an herbicide that inhibits photosynthesis are also known, such as, a triazine (psbA and gs+ genes) and a benzonitrile (nitrilase gene) (see Przbilla et al., 1991. *Plant Cell.* 3:169-174). Nucleotide sequences for nitrilase genes are disclosed in U.S. Pat. No. 4,810,648, and DNA molecules containing these genes are available under ATCC Accession Nos. 53435, 67441, and 67442. Cloning and expression of DNA coding for a glutathione S-transferase is described by Hayes et al. (1992. *Biochem. J.* 285:173).

U.S. Patent Publication No: 20030135879 describes dicamba monooxygenase (DMO) from *Pseudomonas maltophilia*, which is involved in the conversion of a herbicidal form of the herbicide dicamba to a non-toxic 3,6-dichlorosalicylic acid and thus can be used for producing plants tolerant to this herbicide.

The metabolism of chlorophenoxyacetic acids, such as, for example 2,4-D herbicide, is known. Genes or plasmids that contribute to the metabolism of such compounds are described, for example, by Muller et al. (2006. *Appl. Environ. Microbiol.* 72(7):4853-4861), Don and Pemberton (1981. *J Bacteriol* 145(2):681-686), Don et al. (1985. *J Bacteriol* 161(1):85-90) and Evans et al. (1971. *Biochem J* 122(4):543-551).

Acetohydroxy acid synthase, which has been found to make plants that express this enzyme resistant to multiple types of herbicides, has been introduced into a variety of plants. See, Hattori et al., Mol. Gen. Genet., 246:419 (1995). Other genes that confer tolerance to herbicides include a gene encoding a chimeric protein of rat cytochrome P4507A1 and yeast NADPH-cytochrome P450 oxidoreductase (Shiota et al., Plant Physiol., 106:17 (1994)); genes for glutathione reductase and superoxide dismutase (Aono, et al., Plant Cell Physiol., 36:1687 (1995)); and genes for various phosphotransferases (Datta, et al., Plant Mol. Biol., 20:619 (1992)).

Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282,837, 5,767,373, and International Publication WO 01/12825.

Any of the above listed herbicide genes can be introduced into the disclosed 'Georgia-SP/RKN' through a variety of means including but not limited to transformation and crossing.

Disease and Insect Resistance

Plant defenses are often activated by specific interaction between the product of a disease resistance gene (R) in the plant and the product of a corresponding avirulence (Avr) gene in the pathogen. A plant, such as 'Georgia-SP/RKN' or progeny thereof, can be transformed with cloned resistance gene to engineer plants that are resistant to specific pathogen strains. See, for example Jones et al. (1994. Science 266:789) (tomato Cf-9 gene for resistance to *Cladosporium fulvum*); Martin et al. (1993. Science 262(5138):1432-1436) (tomato Pto gene for resistance to *Pseudomonas syringae* pv.); and Mindrinos et al. (1994. *Cell* 78:1089-1099) (*Arabidopsis* RSP2 gene for resistance to *Pseudomonas syringae*).

A viral-invasive protein or a complex toxin derived therefrom can also be used for viral disease resistance. For example, the accumulation of viral coat proteins in transformed plant cells imparts resistance to viral infection and/or disease development effected by the virus from which the coat protein gene is derived, as well as by related viruses. See Beachy et al. (1990. *Annu Rev Phytopathol* 28:451-474). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

A virus-specific antibody can also be used. See, for example, Tavladoraki et al. (1993. *Nature* 366:469-472), which shows that transgenic plants expressing recombinant antibody genes are protected from virus attack.

Logemann et al. (1992. *Bio/Technology* 10:305-308) disclose transgenic plants expressing a barley ribosome-inactivating gene have an increased resistance to fungal disease.

One example of an insect resistance gene includes a *Bacillus thuringiensis* (Bt) protein, a derivative thereof or a synthetic polypeptide modeled thereon (e.g., see Geiser et al., 1986. Gene 48:109, discloses a Bt Δendotoxin gene). Moreover, DNA molecules encoding Δ-endotoxin genes can be obtained from ATCC (Manassas, VA), for example under ATCC Accession Nos. 40098, 67136, 31995 and 31998. Another example is a lectin. See, for example, Van Damme et al. (1994. *Plant Mol Biol* 24(5):825-830), which discloses several *Clivia miniata* mannose-binding lectin genes. A vitamin-binding protein can also be used, such as avidin. See WO 1994/000992, which teaches the use of avidin and avidin homologues as larvicides against insect pests.

In one example the insect resistance gene is an enzyme inhibitor, for example, a protease, proteinase inhibitor, or an α-amylase inhibitor. See, for example, Abe et al. (1987. *J. Biol. Chem.* 262:16793-7; discloses a rice cysteine proteinase inhibitor), Genbank Accession Nos. Z99173.1 and DQ009797.1 which disclose proteinase inhibitor coding sequences, and Sumitani et al. (1993. *Plant Mol. Biol.* 21:985; discloses *Streptomyces nitrosporeus* α-amylase inhibitor). An insect-specific hormone or pheromone can also be used. See, for example, Hammock et al. (1990. *Nature* 344:458-461; discloses juvenile hormone esterase, an inactivator of juvenile hormone).

Still other examples include an insect-specific antibody or an immunotoxin derived therefrom and a developmental-arrestive protein. See Taylor et al. (1994. Seventh Intl. Symposium on Molecular Plant-Microbe Interactions (Edinburgh Scotland), Abstract #497), who described enzymatic inactivation in transgenic tobacco via production of single-chain antibody fragments.

An enzyme inhibitor, for example, a protease or proteinase inhibitor or an amylase inhibitor can be used. See, for example, Abe et al., J. Biol. Chem., 262:16793 (1987) (nucleotide sequence of rice cysteine proteinase inhibitor); Huub et al., Plant Molec. Biol., 21:985 (1993) (nucleotide sequence of cDNA encoding tobacco proteinase inhibitor I); Sumitani et al., Biosci. Biotech. Biochem., 57:1243 (1993) (nucleotide sequence of *Streptomyces nitrosporeus*.alpha.-amylase inhibitor); and U.S. Pat. No. 5,494,813.

An insect-specific hormone or pheromone, such as an ecdysteroid or juvenile hormone, a variant thereof, a mimetic based thereon, or an antagonist or agonist thereof. See, for example, the disclosure by Hammock et al., Nature, 344:458 (1990), of baculovirus expression of cloned juvenile hormone esterase, an inactivator of juvenile hormone.

An insect-specific peptide or neuropeptide which, upon expression, disrupts the physiology of the affected pest. For example, see the disclosures of Regan, J. Biol. Chem., 269:9 (1994) (expression cloning yields DNA coding for insect diuretic hormone receptor); Pratt, et al., Biochem. Biophys. Res. Comm., 163:1243 (1989) (an allostatin is identified in *Diploptera puntata*); Chattopadhyay, et al., Critical Reviews in Microbiology, 30(1):33-54 (2004); Zjawiony, J Nat Prod, 67(2):300-310 (2004); Carlini & Grossi-de-Sa, Toxicon, 40(11):1515-1539 (2002); Ussuf, et al., Curr Sci., 80(7): 847-853 (2001); Vasconcelos & Oliveira, Toxicon, 44(4): 385-403 (2004). See also, U.S. Pat. No. 5,266,317 to Tomalski, et al., which discloses genes encoding insect-specific, paralytic neurotoxins.

An insect-specific venom produced in nature by a snake, a wasp, etc. For example, see, Pang, et al., Gene, 116:165 (1992), for disclosure of heterologous expression in plants of a gene coding for a scorpion insectotoxic peptide.

An enzyme responsible for a hyperaccumulation of a monoterpene, a sesquiterpene, a steroid, hydroxamic acid, a phenylpropanoid derivative, or another non-protein molecule with insecticidal activity.

An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See, PCT Application WO 93/02197, which discloses the nucleotide sequence of a callase gene. DNA molecules which contain chitinase-encoding sequences can be obtained, for example, from the ATCC under Accession Nos. 39637 and 67152. See also, Kramer, et al., Insect Biochem. Molec. Biol., 23:691 (1993), who teach the nucleotide sequence of a cDNA encoding tobacco hornworm chitinase, and Kawalleck, et al., Plant Molec. Biol., 21:673 (1993), who provide the nucleotide sequence of the parsley ubi4-2 polyubiquitin gene, U.S. Pat. Nos. 7,145,060, 7,087,810, and 6,563,020.

A molecule that stimulates signal transduction. For example, see the disclosure by Botella, et al., Plant Molec. Biol., 24:757 (1994), of nucleotide sequences for mung bean calmodulin cDNA clones, and Griess, et al., Plant Physiol., 104:1467 (1994), who provide the nucleotide sequence of a maize calmodulin cDNA clone.

A hydrophobic moment peptide. See, PCT Application WO 95/16776 and U.S. Pat. No. 5,580,852, which disclose peptide derivatives of tachyplesin which inhibit fungal plant pathogens, and PCT Application WO 95/18855 and U.S. Pat. No. 5,607,914 which teaches synthetic antimicrobial peptides that confer disease resistance.

A membrane permease, a channel former or a channel blocker. For example, see the disclosure of Jaynes, et al., Plant Sci, 89:43 (1993), of heterologous expression of a cecropin-beta lytic peptide analog to render transgenic tobacco plants resistant to *Pseudomonas solanacearum*.

A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., Ann. Rev. Phytopathol., 28:451 (1990). Coat protein-mediated resistance has been conferred upon transformed plants against alfalfa mosaic virus, cucumber mosaic virus, and tobacco mosaic virus.

An insect-specific antibody or an immunotoxin derived therefrom. Thus, an antibody targeted to a critical metabolic function in the insect gut would inactivate an affected enzyme, killing the insect. See, Taylor, et al., Abstract #497, Seventh Int'l Symposium on Molecular Plant-Microbe Interactions (Edinburgh, Scotland 1994) (enzymatic inactivation in transgenic tobacco via production of single-chain antibody fragments).

A virus-specific antibody. See, for example, Tavladoraki et al., Nature, 366:469 (1993), who show that transgenic plants expressing recombinant antibody genes are protected from virus attack.

A developmental-arrestive protein produced in nature by a pathogen or a parasite. Thus, fungal endo-.alpha.-1,4-D-polygalacturonases facilitate fungal colonization and plant nutrient release by solubilizing plant cell wall homo-.alpha.-1,4-D-galacturonase. See, Lamb, et al., Bio/Technology, 10:1436 (1992). The cloning and characterization of a gene which encodes a bean endopolygalacturonase-inhibiting protein is described by Toubart, et al., Plant J., 2:367 (1992).

A developmental-arrestive protein produced in nature by a plant. For example, Logemann, et al., Bio/Technology, 10:305 (1992), have shown that transgenic plants expressing the barley ribosome-inactivating gene have an increased resistance to fungal disease.

Genes involved in the Systemic Acquired Resistance (SAR) Response and/or the pathogenesis-related genes. Briggs, S., Current Biology, 5(2) (1995); Pieterse & Van Loon, Curr. Opin. Plant Bio., 7(4):456-64 (2004); and Somssich, Cell, 113(7):815-6 (2003).

Antifungal genes. See, Cornelissen and Melchers, Plant Physiol., 101:709-712 (1993); Parijs, et al., Planta, 183:258-264 (1991); and Bushnell, et al., Can. J. of Plant Path., 20(2):137-149 (1998). See also, U.S. Pat. No. 6,875,907.

Detoxification genes, such as for fumonisin, beauvericin, moniliformin, and zearalenone and their structurally-related derivatives. See, for example, U.S. Pat. No. 5,792,931.

Cystatin and cysteine proteinase inhibitors. See, U.S. Pat. No. 7,205,453.

Defensin genes. See, WO 03/000863 and U.S. Pat. No. 6,911,577.

Genes conferring resistance to nematodes, such as root-knot nematode and root lesion nematode. See, e.g., WO 96/30517, WO 93/19181, and WO 03/033651; Urwin et al., Planta, 204:472-479 (1998); Williamson, Curr Opin Plant Bio., 2(4):327-31 (1999).

Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7, and other Rps genes.

Genes that confer resistance to Brown Stem Rot, such as described in U.S. Pat. No. 5,689,035 and incorporated by reference for this purpose.

Any of the above-listed disease or pest resistance genes can be introduced into 'Georgia-SP/RKN' through a variety of means including, but not limited to, transformation and crossing.

Male Sterility

Genetic male sterility can increase the efficiency with which hybrids are made, in that it can eliminate the need to physically emasculate the peanut plant used as a female in a given cross (Brim and Stuber. 1973. *Crop Sci.* 13:528-530). Herbicide-inducible male sterility systems are known (e.g., U.S. Pat. No. 6,762,344).

Where use of male-sterility systems is desired, it can be beneficial to also utilize one or more male-fertility restorer genes. For example, where cytoplasmic male sterility (CMS) is used, hybrid seed production involves three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful where the vegetative tissue of the peanut plant is utilized. However, in many cases, the seeds are considered to be a valuable portion of the crop, thus, it is desirable to restore the fertility of the hybrids in these crops. Therefore, the disclosure provides plants of the new peanut variety 'Georgia-SP/RKN' comprising a genetic locus capable of restoring male fertility in an otherwise male-sterile plant. Examples of male-sterility genes and corresponding restorers which can be employed are known (see, e.g., U.S. Pat. Nos. 5,530,191 and 5,684,242).

There are several methods of conferring genetic male sterility available, such as multiple mutant genes at separate locations within the genome that confer male sterility, as disclosed in U.S. Pat. Nos. 4,654,465 and 4,727,219 and chromosomal translocations as described in U.S. Pat. Nos. 3,861,709 and 3,710,511. In addition to these methods, U.S. Pat. No. 5,432,068, describes a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on," the promoter, which in turn allows the gene that confers male fertility to be transcribed.

Introduction of a deacetylase gene under the control of a tapetum-specific promoter and with the application of the chemical N—Ac-PPT. See WO 01/29237.

Introduction of various stamen-specific promoters. See WO 92/13956 and WO 92/13957.

Introduction of the barnase and the barstar genes. See, Paul et al., Plant Mol. Biol., 19:611-622 (1992).

For additional examples of nuclear male and female sterility systems and genes, see also, U.S. Pat. Nos. 5,859,341, 6,297,426, 5,478,369, 5,824,524, 5,850,014, and 6,265,640.

Any of the above-listed male sterility genes can be introduced into 'Georgia-SP/RKN' through a variety of means including, but not limited to, transformation and crossing.

Exemplary Genes that Confer a Value-Added Trait

Genes conferring modified fatty acid metabolism can be introduced into 'Georgia-SP/RKN' and its progeny, such as antisense stearoyl acyl carrier protein (ACP) desaturase genes (EC 1.14.99.6) (e.g., Knutzon et al. 1992. PNAS 89:2624-2628). Fatty acid desaturases can be introduced into 'Georgia-SP/RKN' and its progeny, such as *Saccharomyces cerevisiae* OLE1 gene encoding Δ9-fatty acid desaturase, an enzyme which forms the monounsaturated palmitoleic (16:1) and oleic (18:1) fatty acids from palmitoyl (16:0) or stearoyl (18:0) CoA (McDonough et al., 1992. *J Biol Chem* 267(9):5931-5936); a gene encoding a stearoyl-acyl carrier protein Δ-9 desaturase from castor (Fox et al. 1993. *PNAS* 90(6):2486-2490); Δ 6- and Δ12-desaturases from the cyanobacteria *Synechocystis* responsible for the conversion of linoleic acid (18:2) to gamma-linolenic acid (18:3 gamma) (Reddy et al., 1993. *Plant Mol Biol* 22(2):293-300); a gene from *Arabidopsis thaliana* that encodes an omega-3 desaturase (Arondel et al. 1992. Science 258:1353-

5); plant Δ 9-desaturases (WIPO Publication No. WO 1991/013972) and peanut and *Brassica* Δ15 desaturases (European Patent Application Publ. No. EP 0616644).

Phytate metabolism can also be modified by introduction of a phytase-encoding gene to enhance breakdown of phytate, adding more free phosphate to the transformed plant. For example, see Van Hartingsveldt et al. (1993. *Gene* 127:87-94), for an *Aspergillus niger* phytase gene. In peanut, this, for example, could be accomplished by cloning and then reintroducing DNA associated with the single allele which is responsible for peanut mutants characterized by low levels of phytic acid. See Raboy et al. (2000*, Plant Physiol.* 124(1):355-68).

A number of genes can be used to alter carbohydrate metabolism. For example, plants can be transformed with a gene coding for an enzyme that alters the branching pattern of starch or a gene altering thioredoxin, such as NTR and/or TRX (see, U.S. Pat. No. 6,531,648), and/or a gamma zein knock out or mutant, such as cs27 or TUSC27 or en27 (see, U.S. Pat. No. 6,858,778, and U.S. Publ. Nos. 2005/0160488 and 2005/0204418). See, Shiroza et al. (1988. *J Bacteriol* 170(2):810-816) (*Streptococcus* fructosyltransferase gene), Steinmetz et al. (1985. Mol Gen Genet. 200:220-228) (*Bacillus subtilis* levansucrase gene), Pen et al. (1992. *BioTechnology* 10:292) (*Bacillus licheniformis* α-amylase), Elliot et al. (1993. *Plant Mol. Biol* 21:515) (tomato invertase genes), Sergaard et al. (1993. *J. Biol. Chem.* 268:22480) (site-directed mutagenesis of barley α-amylase gene), and Fisher et al. (1993. *Plant Physiol* 102:1045) (maize endosperm starch branching enzyme II), WO 99/10498 (improved digestibility and/or starch extraction through modification of UDP-D-xylose 4-epimerase, Fragile 1 and 2, Ref 1, HCHL, C4H); U.S. Pat. No. 6,232,529 (method of producing high oil seed by modification of starch levels (AGP)). The fatty acid modification genes mentioned above may also be used to affect starch content and/or composition through the interrelationship of the starch and oil pathways. The Z10 gene encoding a 10 kD zein storage protein from maize can also be used to alter the quantities of 10 kD zein in the cells relative to other components (Kirihara et al., 1988. *Mol Gen Genet.* 211:477-484).

Although the 'Georgia-SP/RKN' plants of the present application have high oleic acid concentration in the seed oil, additional gene modifications can be made to further increase oleic acid and/or decrease linoleic acid. For instance, elevated oleic acid via FAD-2 gene modification and/or decreased linolenic acid via FAD-3 gene modification can be implemented. See, U.S. Pat. Nos. 6,063,947, 6,323,392, and WO 93/11245. Although as many as 12 fatty acids have been reported in peanuts, only 3 are present in amounts exceeding 5%: palmitic, oleic and linoleic (Ahmed et al., in Peanut Science and Technology (1982 H. E. Pattec, et al., ed)). These three fatty acids comprise about 90% of the fatty acid composition of the oil, with oleic and linoleic comprising about 80%. The remainder of the fatty acids comprise about 10%, each ranging in concentration from 0.02% to 2.59%. The American Heart Association and the American Health Foundation have recommended diet modifications to achieve lower serum cholesterol levels in the population. These diet modifications include reducing consumption of saturated fatty acids and thereby increasing the polyunsaturated to saturated (P/S) ratio in the diet (Technical Committee, Food Fats and Oils, 5.sup.th ed. (1992)). Edible peanut oils with a higher percentage of unsaturated fatty acids can be used for these cardio-vascular health reasons (Mattson et al., J Lipid Research 26:194-202 (1985)).

Altering conjugated linolenic or linoleic acid content, such as in WO 01/12800. Altering LEC1, AGP, Dek1, Superal1, mi1ps, and various Ipa genes, such as Ipa1, Ipa3, hpt, or hggt. See, for example, WO 02/42424, WO 98/22604, WO 03/011015, WO 02/057439, WO 03/011015, U.S. Pat. Nos. 6,423,886, 6,197,561, 6,825,397, 7,157,621, U.S. Publ. No. 2003/0079247, and Rivera-Madrid et al., Proc. Natl. Acad. Sci., 92:5620-5624 (1995).

Altered antioxidant content or composition, such as alteration of tocopherol or tocotrienols. See, for example, U.S. Pat. Nos. 6,787,683, 7,154,029, WO 00/68393 (involving the manipulation of antioxidant levels through alteration of a phytl prenyl transferase (ppt)); WO 03/082899 (through alteration of a homogentisate geranyl geranyl transferase (hggt)).

Altered essential seed amino acids. See, for example, U.S. Pat. No. 6,127,600 (method of increasing accumulation of essential amino acids in seeds); U.S. Pat. No. 6,080,913 (binary methods of increasing accumulation of essential amino acids in seeds); U.S. Pat. No. 5,990,389 (high lysine); U.S. Pat. No. 5,850,016 (alteration of amino acid compositions in seeds); U.S. Pat. No. 5,885,802 (high methionine); U.S. Pat. No. 5,885,801 (high threonine); U.S. Pat. No. 6,664,445 (plant amino acid biosynthetic enzymes); U.S. Pat. No. 6,459,019 (increased lysine and threonine); U.S. Pat. No. 6,441,274 (plant tryptophan synthase beta subunit); U.S. Pat. No. 6,346,403 (methionine metabolic enzymes); U.S. Pat. No. 5,939,599 (high sulfur); U.S. Pat. No. 5,912,414 (increased methionine); U.S. Pat. No. 5,633,436 (increasing sulfur amino acid content); U.S. Pat. No. 5,559,223 (synthetic storage proteins with defined structure containing programmable levels of essential amino acids for improvement of the nutritional value of plants); U.S. Pat. No. 6,194,638 (hemicellulose); U.S. Pat. No. 7,098,381 (UDPGdH); U.S. Pat. No. 6,194,638 (RGP); U.S. Pat. Nos. 6,399,859, 6,930,225, 7,179,955, and 6,803,498; U.S. Publ. No. 2004/0068767; WO 99/40209 (alteration of amino acid compositions in seeds); WO 99/29882 (methods for altering amino acid content of proteins); WO 98/20133 (proteins with enhanced levels of essential amino acids); WO 98/56935 (plant amino acid biosynthetic enzymes); WO 98/45458 (engineered seed protein having higher percentage of essential amino acids); WO 98/42831 (increased lysine); WO 96/01905 (increased threonine); WO 95/15392 (increased lysine); WO 01/79516; and WO 00/09706 (Ces A: cellulose synthase).

Any of the above-listed value-added trait genes can be introduced into 'Georgia-SP/RKN' through a variety of means including, but not limited to, transformation and crossing.

Genes that Create a Site for Site Specific DNA Integration

This includes the introduction of FRT sites that may be used in the FLP/FRT system and/or Lox sites that may be used in the Cre/Loxp system. See, for example, Lyznik, et al., Site-Specific Recombination for Genetic Engineering in Plants, Plant Cell Rep, 21:925-932 (2003) and WO 99/25821, which are hereby incorporated by reference. Other systems that may be used include the Gin recombinase of phage Mu (Maeser, et al. (1991); Vicki Chandler, The Maize Handbook, Ch. 118 (Springer-Verlag 1994)); the Pin recombinase of *E. coli* (Enomoto, et al. (1983)); and the R/RS system of the pSR1 plasmid (Araki, et al. (1992)).

Any of the above-listed sites can be introduced into 'Georgia-SP/RKN' through a variety of means including, but not limited to, transformation and crossing.

Genes that Affect Abiotic Stress Resistance

Genes that affect abiotic stress resistance (including but not limited to flowering, pod and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; U.S. Publ. No. 2004/0148654 and WO 01/36596, where abscisic acid is altered in plants resulting in improved plant phenotype, such as increased yield and/or increased tolerance to abiotic stress; WO 2000/006341, WO 04/090143, U.S. Pat. Nos. 7,531,723, and 6,992,237, where cytokinin expression is modified resulting in plants with increased stress tolerance, such as drought tolerance, and/or increased yield. See also, WO 02/02776, WO 2003/052063, JP 2002281975, U.S. Pat. No. 6,084,153, WO 01/64898, and U.S. Pat. Nos. 6,177,275 and 6,107,547 (enhancement of nitrogen utilization and altered nitrogen responsiveness). For ethylene alteration, see, U.S. Publ. Nos. 2004/0128719, 2003/0166197, and WO 2000/32761. For plant transcription factors or transcriptional regulators of abiotic stress, see, e.g., U.S. Publ. Nos. 2004/0098764 or 2004/0078852.

Other genes and transcription factors that affect plant growth and agronomic traits, such as yield, flowering, plant growth, and/or plant structure, can be introduced or introgressed into plants. See, e.g., WO 97/49811 (LHY), WO 98/56918 (ESD4), WO 97/10339, U.S. Pat. No. 6,573,430 (TFL), 6,713,663 (FT), 6,794,560, 6,307,126 (GAI), WO 96/14414 (CON), WO 96/38560, WO 01/21822 (VRN1), WO 00/44918 (VRN2), WO 99/49064 (GI), WO 00/46358 (FR1), WO 97/29123, WO 99/09174 (D8 and Rht), WO 2004/076638, and WO 004/031349 (transcription factors).

Any of the above-listed sites can be introduced into 'Georgia-SP/RKN' through a variety of means including, but not limited to, transformation and crossing.

Tissue Cultures and In Vitro Regeneration of Peanut Plants

Tissue cultures of the new peanut variety 'Georgia-SP/RKN', such as tissue cultures obtained from a peanut plant of peanut variety 'Georgia-SP/RKN' grown from a seed of peanut variety 'Georgia-SP/RKN' ATCC Accession No. PTA-127584 (NPGS PI No. PI #700991). are provided. Further reproduction of the 'Georgia-SP/RKN' and its progeny can occur by tissue culture and regeneration. Tissue culture of various tissues of peanuts and regeneration of plants there from is known. For example, see Komatsuda et al., Crop Sci., 31:333-337 (1991); Stephens et al., Theor. Appl. Genet., 82:633-635 (1991); Komatsuda, et al., Plant Cell, Tissue and Organ Culture, 28:103-113 (1992); Dhir et al., Plant Cell Reports, 11:285-289 (1992); Pandey et al., Japan J. Breed., 42:1-5 (1992); and Shetty et al., Plant Science, 81:245-251 (1992); as well as U.S. Pat. Nos. 5,024,944, and 5,008,200, issued. Thus, provided are cells, which upon growth and differentiation produce peanut plants having the physiological and morphological characteristics of peanut cultivar 'Georgia-SP/RKN'.

A tissue culture includes isolated cells of the same or a different type or a collection of such cells organized into parts of a plant. Exemplary types of tissue cultures include protoplasts, calli and plant cells that are intact in plants or parts of plants, such as embryos, pollen, flowers, leaves, roots, root tips, anthers, meristematic cells, pistil, seed, pod, petiole, stein, ovule, cotyledon, hypocotyl, shoot, stem, and the like. In a particular example, the tissue culture includes embryos, protoplasts, meristematic cells, pollen, leaves or anthers of the new peanut variety 'Georgia-SP/RKN'. Also provided are peanut plants regenerated from such tissue cultures, wherein the regenerated peanut plant expresses the physiological and morphological characteristics of the peanut variety 'Georgia-SP/RKN'.

Exemplary methods for preparing and maintaining plant tissue culture are described in. U.S. Pat. Nos. 5,959,185, 5,973,234, and 5,977,445.

Example 1

Breeding History of 'Georgia-SP/RKN'

'Georgia-SP/RKN' is a new high-oleic, peanut root-knot nematode [*Meloidogyne arenaria* (Neal)] (RKN) resistant, and Tomato spotted wilt virus (TSWV) resistant, large-seeded spanish market-type peanut (*Arachis hypogaea* L. subsp. *hypogaea* var. *hypogaea*) cultivar. It was developed at a research farm in Tifton, Georgia.

'Georgia-SP/RKN' (tested as GA 082549R-2) was derived from an individual plant selection made from the cultivar 'Georgia-17SP' (PI #687138, protected by PVP, application #201800511). Details on the breeding history of 'Georgia-17SP' and 'Georgia-SP/RKN') are found in Table A. 'Georgia-17SP' was derived from a cross made in winter of 2003/2004 between 'Georgia-02C' (PI #632380, protected by PVP, application #200300051) and an $F_4$ selection from a population developed by crossing 'Georgia-01R' (PI #629027, protected by PVP, application #200200171) and 'COAN' (PI #610452, PVP certificate expired, application #9900338) (the parentage of 'Georgia-17SP' is indicated as "Georgia-02C/Georgia-01R/COAN"). 'Georgia-02C' is a high-oleic runner-type peanut cultivar with medium-plus maturity (~147 days) and spreading runner growth habit. 'Georgia-01R' is a runner-type peanut cultivar with excellent general disease resistance and medium-late maturity (~154-160 days) with spreading runner growth habit. 'COAN', developed by the Texas Agricultural Experiment Station was the first peanut cultivar with a high level of resistance to peanut root-knot nematode [*Meloidogyne arenaria* (Neal)] (RKN). 'COAN' was derived by backcrossing recurrent parent, 'Florunner' (PI #565448), five times with the interspecific hybrid germplasm line, 'TxAG-6' (PI #565287).

TABLE A

| PEDIGREE SELECTION METHOD | |
|---|---|
| 2003/2004 | 'GA-02C' × $F_4$ selection of ('Georgia-01R' × 'COAN') |
| 2004 | $F_1$ seed from cross above planted in Tifton, GA |
| 2004-2007 | Pedigree-based selection from $F_2$-$F_4$ generation |
| 2008-2017 | $F_{4:5}$ Progeny Row harvested, generations $F_{5:n}$ considered pure-line and tested as GA 082549 until release as 'Georgia-17SP' |
| 2016 | RKN-resistant individual plant selections made from 'Georgia-17SP' in RKN-infested field trial |

TABLE A-continued

| PEDIGREE SELECTION METHOD | |
|---|---|
| 2017 | Progeny rows of RKN-resistant individual plant selections were grown for seed increase |
| 2018-2021 | Replicated, multi-environmental testing to confirm phenotypic resistance of new 'Georgia-SP/RKN' to RKN and confirm agronomic performance |

The $F_1$ seed from the cross 'GA-02C'×$F_4$ selection of ('Georgia-01R'×'COAN') were space-planted in 2004 at a research farm located in Tifton, GA. Pedigree-based selection method for peanut breeding (Knauft et al., 1987. Peanut. Pp. 346-384. In W. R. Fehr (ed.). Principles of Cultivar Development. Vol. 2. Crop Species. Macmillan Publishing Co. New York.) was carried out on individual plants within the $F_2$, $F_3$, and $F_4$ generation. Individual plants were selected each year, the best individual plant was advanced to plant the progeny row for each successive year. Thus, GA 082549 was derived from a single $F_1$ plant in 2004, a single $F_2$ plant in 2005, and so forth until the final $F_4$ individual plant was harvested. The $F_4$ individual-plant-derived, $F_5$ progeny row constituted the line, GA 082549, and was grown in 2008. The $F_{4:5}$ progeny row was bulk-harvested, considered a pure-line in subsequent generations, and tested with replicated, multi-environmental testing from 2008-2017 as GA 082549 until its release in 2017 as 'Georgia-17SP'.

During the 2008-2016 multi-environmental testing, 'Georgia-17SP' was identified as partially resistant to RKN, and it was decided to work toward improving that RKN resistance by making pure-line selections from 'Georgia-17SP'. Beginning in 2016, based upon phenotypic observation and DNA marker results using tightly linked markers, RKN-resistant individual plant selections were made from within 'Georgia-17SP' in a RKN-infested field trial. The resulting progeny rows were grown in 2017 for seed increase. Replicated yield trials were carried out in 2018-2021 under optimum growing conditions and in a RKN-infested field in 2019 to confirm phenotypic resistance to RKN. Visual evaluations were made in seed increase plots every year from 2018-2021 and with multi-location testing to confirm stability and performance of RKN resistance in nematode-free and nematode infested locations and to confirm uniformity and other traits. DNA-marker screening was performed to confirm the presence of root-knot nematode resistance gene (data not shown, but see FIG. 1). Gas chromatography testing of seed was performed to confirm high oleic fatty acid concentration in seed oil.

'Georgia-SP/RKN' was developed using the pedigree selection method for peanut breeding (Knauft et al., 1987. Peanut. Pp. 346-384. In W. R. Fehr (ed.). Principles of Cultivar Development. Vol. 2. Crop Species. Macmillan Publishing Co. New York.). Briefly, the $F_0$ hybrid seed was created in a greenhouse by crossing 'Georgia-02C' with an $F_4$ selection derived from crossing 'Georgia-01R' and 'COAN'. Up to five of the resulting $F_0$ hybrid seed were hand-planted in a 6.1 m by 0.8 m plot, with individual seeds spaced 1.2 m apart in a row for the $F_1$ nursery. A single $F_1$ plant was selected from this nursery for advancement. The resulting seeds were used to plant the $F_2$ nursery, in which seeds were planted 0.3 m apart in paired rows spaced 0.8 m apart on 1.8 m beds up to 30.5 m long. Nursery plots are typically planted in this manner, although plot length can vary from year to year. Individual plants are selected visually in the field for a number of agronomic traits including yield and pod characteristics, and then further selected based on shelling characteristics, chemical composition, or other traits. A single plant from the $F_2$ nursery was selected for planting the $F_3$ progeny row. From the $F_3$ progeny row, a single plant was advanced for the $F_4$ progeny row nursery. From the $F_4$ progeny row, a single plant was selected for planting the $F_5$ progeny rows. Multiple 20' plots of the $F_4$-derived $F_5$ ($F_4$:5) progeny rows were planted. These $F_5$ plots were bulk-harvested and the seed used for planting replicated yield trials. Replicated testing was conducted under maximum and minimum input production scenarios and across a range of environments. Yield trial plots were 6.1 m long, two rows wide with rows spaced 0.8 m apart within a plot on beds 1.8 m wide. Seeds were spaced approximately 5.1 cm apart. During the testing of Georgia-17SP, it was realized that it had partial resistance to RKN. To improve upon that level of resistance, plots of Georgia-17SP were planted in a RKN-infested field, and resistant individual plants were selected. Progeny rows derived from these individual plants were grown in 2017 for seed increase. Replicated yield testing was conducted from 2018 to 2021 to ensure agronomic performance and uniformly high RKN-resistance. The breeding line GA 082549R-2 was selected from these trials for release as cultivar Georgia-SP/RKN.

Example 2

Description of 'Georgia-SP/RKN'

'Georgia-SP/RKN' is unique from other spanish market-type peanut cultivars at least in having a combination of high-oleic content, medium-plus maturity (about 147-150 days to maturity), high level of resistance to peanut root-knot nematode [*Meloidogyne arenaria* (Neal)] (RKN), and a high level of TSWV resistance. Georgia-SP/RKN is a high-yielding, high-oleic, large-seeded spanish market type peanut cultivar with intermediate decumbent runner growth habit, tan testa color, medium-plus maturity (147-150 days to maturity) and is highly resistant to peanut root-knot nematode [*Meloidogyne arenaria* (Neal)] (RKN). Georgia-SP/RKN is similar to 'Georgia-17SP' for many of the phenotypic traits measured in replicated trials from 2018-2021, except that Georgia-SP/RKN has a very high level of RKN-resistance. Georgia-SP/RKN is distinct from most spanish market type peanut cultivars in that it is well-adapted to southeastern growing conditions, has a high level of TSWV resistance, and a very high level of resistance to RKN.

Additionally, the introgressed segment on chromosome A09 that conveys RKN-resistance in Georgia-SP/RKN is a greatly reduced introgressed segment of DNA from TxAG-6 compared to other RKN-resistant cultivars such as 'Georgia-14N'. FIG. 1 shows a visual representation of GBS-based SNP genotyping results of chromosome (Chr.) A09 (light gray) for RKN-resistant cultivars 'Georgia-14N' and 'Georgia-SP/RKN' compared to RKN-susceptible cultivar 'Georgia-06G'. As illustrated in FIG. 1, the TxAG-6 introgression (dark gray/blk) in Georgia-SP/RKN represents about 3% or less (e.g., 3.5 Mb, or 2.9%) of the total A09 chromosome compared to the 8 Mb, or 6.7% in 'Georgia-14N'.

Testing of characteristics such as yield, value, disease susceptibility, specific resistance to TSWV and RKN, and other agronomic traits of 'Georgia-SP/RKN' in comparison to other varieties were determined from replicated field trials over 4 years (2018-2021) at multiple locations in Georgia. Details of the various trials, tests, and comparisons are provided below and in the following Examples.

Plots were 2 rows wide, 6.1 m long×1.8 m wide with row spacing of about 0.8 m within rows and about 1.0 m between rows on adjacent plots. Tests were planted between mid-April and mid-May at 0.2 seed $cm^{-1}$. Production practices included conventional tillage, fertilization, recommended pesticides and rates, irrigated, and non-irrigated. These field trials were in a three-year rotation following cotton (*Gossypium* ssp.) and corn (*Zea mays* L.). Entries were dug near optimum maturity each year based upon hull-scrape determination from adjacent border plots (Williams and Drexler, Peanut Sci., 8:134-41, 1981).

After digging and picking, pods were dried with forced warm air to 6% moisture. Pod samples were then hand-cleaned over a screen table before weighing for yield, shelling, and grading. In the grading process, total sound mature kernels (TSMK) equal the sum of sound mature kernels (SMK) and sound splits (SS). Sound mature kernels equals the percentage of sound mature seed excluding damaged and split seed riding a minimum slotted screen size of 5.95 mm in width.

Data for each variable were subjected to analysis of variance (ANOVA). Waller-Duncan's Bayesian t-Test (k-ratio=100) was used for mean separation involving three or more entries (Tables 1-10).

In summary, 'Georgia-SP/RKN' was found to be a high yielding, high-oleic, highly RKN-resistant spanish market type peanut cultivar that can provide a good option for peanut growers targeting the confectionary peanut market, especially for growers in the lower southeastern US. The high level of RKN-resistance, high TSWV resistance, high dollar value returns, and adaptation to a longer growing season make Georgia-SP/RKN better-suited for Southeastern growers than the spanish cultivars that are currently available.

Example 3

Pod Yield and Dollar Value

Across the 4 testing environments (April and May planted trails in Tifton in 2020 and 2021; 4 trials total) in which spanish cultivar trials were planted in 2020 and 2021, 'Georgia-SP/RKN' exhibited pod yields (Table 1) similar to 'Georgia-04S' and 'Georgia-17SP' and higher than 'Georgia Browne', 'Tamnut OL06', 'Ole', and 'OLin'. A significant interaction of cultivar x environment was evident in the combined analysis of variance. Consequently, pod yields are also reported by testing environment. Georgia-SP/RKN was within the highest pod yield significance grouping in April-planted trials. However, in May-planted trials, 'Georgia-04S' was higher-yielding in 2020. In May-planted trials in 2021, 'Georgia-04S' and 'Georgia Browne' were higher yielding than Georgia-SP/RKN. 'Georgia Browne' exhibited uncharacteristically high pod yield in the May-planted test in 2021, likely contributing to the significant interaction of cultivar x environment.

Dollar values were calculated upon USDA peanut loan schedules for each crop year, and were based upon yield and grade factors to obtain a gross dollar value return per hectare. Dollar values (Table 2) were the same for 'Georgia-04S', Georgia-SP/RKN, and 'Georgia-17SP' across the four testing environments (Table 2). Georgia-SP/RKN was in the highest dollar value significance grouping for each test except for the May-planted trial in 2021

TABLE 1

Pod yield comparisons of spanish cultivars in four trials planted in mid-April and mid-May from 2020 to 2021 at Tifton, GA.

| | 2020 | | 2021 | | |
|---|---|---|---|---|---|
| Cultivar | April | May | April | May | Average |
| | kg/ha | kg/ha | kg/ha | kg/ha | kg/ha |
| 'Georgia-04S' | 3840 b | 3829 a | 3265 b | 5904 a | 4317 a |
| Georgia-SP/RKN | 4144 a | 3491 b | 4050 a | 5011 b | 4188 ab |
| 'Georgia-17SP' | 4214 a | 3291 bc | 4223 a | 4828 b | 4127 bc |
| 'Georgia Browne' | 3609 b | 3116 c | 2857 bc | 5863 a | 3969 c |
| 'Tamnut OL06' | 2936 c | 3004 c | 3190 b | 4964 b | 3583 d |
| 'Olé' | 3108 c | 2459 d | 2690 bc | 3797 c | 3040 e |
| 'Olin' | 2082 d | 2322 d | 2458 c | 4137 c | 2809 f |
| CV % | 5.82 | 8.76 | 13.42 | 7.46 | 8.67 |

† Values within columns followed by the same letter are not different at Waller-Duncan kratio = 100.

TABLE 2

Dollar value comparisons for four spanish cultivar trials planted in mid-April and mid-May from 2020 to 2021 at Tifton, GA.

| | 2020 | | 2021 | | |
|---|---|---|---|---|---|
| Cultivar | April | May | April | May | Average |
| | $/ha | $/ha | $/ha | $/ha | $/ha |
| 'Georgia-04S' | 1491 b† | 1521 a | 1274 b | 2349 a | 1703 a |
| Georgia-SP/RKN | 1650 a | 1417 ab | 1638 a | 2052 b | 1696 a |
| 'Georgia-17SP' | 1662 a | 1381 b | 1683 a | 1959 bc | 1671 a |
| 'Georgia Browne' | 1387 c | 1249 c | 1123 bc | 2302 a | 1559 b |
| 'Tamnut OL06' | 1036 d | 1090 d | 1034 cd | 1835 c | 1279 c |
| 'Olé' | 1102 d | 890 e | 926 cd | 1307 e | 1066 d |
| 'Olin' | 741 e | 861 e | 835 d | 1558 d | 1027 d |
| CV % | 5.8 | 8.7 | 13.5 | 7.6 | 8.7 |

†Values within columns followed by the same letter are not different at Waller-Duncan kratio = 100.

Example 4

Mid-Season TSWV Susceptibility and Late-Season Total Disease Susceptibility

Disease incidence of tomato spotted wilt virus (TSWV) was first assessed at midseason, when TSWV is usually the only disease occurring at this time during the growing season. Percentages (0-100%) of total disease (TD) incidence were scored prior to digging. Total disease rating involves visually identifying disease symptoms in each plot. At the end of the season it can be difficult to unequivocally identify the causal disease for dead plants, however, these trials were conducted under a thorough fungicide program, so the primary disease present was TSWV. A disease hit equaled a 30.5-cm section of row containing one or more symptomatic or dead plants.

Mid-season TSWV ratings showed no significant differences for April-planted trials, but May-planted trials showed Georgia-SP/RKN to be among the least susceptible spanish cultivars in 2020 and 2021 (Table 3). Across testing environments, Georgia-SP/RKN showed the best resistance to TSWV, with significantly lower ratings than Georgia Browne, OLin, Tamnut OL06, and OLé.

TABLE 3

Tomato spotted wilt virus susceptibility percentage evaluated at mid-season for four spanish cultivar trials planted in mid-April and mid-May from 2020 to 2021 at Tifton, GA.

| Cultivar | 2020 April | 2020 May | 2021 April | 2021 May | Average |
|---|---|---|---|---|---|
| | % | % | % | % | % |
| OLé | 4.6† | 7.0 ab | 8.3 | 6.7 a | 6.6 a |
| Tamnut OL06 | 5.0 | 6.2 bc | 6.0 | 7.8 a | 6.3 ab |
| OLin | 3.2 | 8.7 a | 3.8 | 4.8 b | 5.3 bc |
| Georgia Browne | 3.6 | 3.8 cd | 7.0 | 3.2 c | 4.2 cd |
| Georgia-17SP | 2.4 | 3.0 d | 2.5 | 4.8 b | 3.3 de |
| Georgia-04S | 2.8 | 3.2 d | 4.3 | 3.0 c | 3.2 de |
| Georgia-SP/RKN | 1.8 | 2.7 d | 2.3 | 4.2 bc | 2.8 e |
| CV % | 56.3 | 43.1 | 63.3 | 28.0 | 46.2 |

†Values within columns followed by the same letter are not different at Waller-Duncan kratio = 100.

Total disease, which is evaluated close to harvest, is a measure of all diseases present. Because a thorough fungicide program was used each year, the primary disease present was TSWV at the end of the growing season. Georgia-SP/RKN was among the cultivars with the lowest TD ratings for each testing environment (Table 4). Georgia-SP/RKN and Georgia-17SP had the lowest total disease ratings across the four spanish cultivar testing environments, indicating a high level of resistance to TSWV.

TABLE 4

Late-season, total disease susceptibility percentage evaluated at harvest, with tomato spotted wilt virus the primary pathogen present, for four Spanish cultivar trials planted in mid-April and mid-May from 2020 to 2021 at Tifton, GA.

| Cultivar | 2020 April | 2020 May | 2021 April | 2021 May | Average |
|---|---|---|---|---|---|
| | % | % | % | % | % |
| Tamnut OL06 | 16.6 a† | 14.2 a | 16.3 bc | 13.8 a | 15.0 a |
| OLé | 17.0 a | 9.8 b | 21.3 ab | 13.0 a | 14.6 a |
| OLin | 15.0 a | 10.7 b | 15.0 bc | 9.2 b | 12.1 b |
| Georgia Browne | 10.8 b | 4.2 c | 25.3 a | 4.3 c | 9.8 c |
| Georgia-04S | 4.2 c | 2.5 c | 16.3 bc | 3.8 c | 5.9 d |
| Georgia-17SP | 2.8 c | 2.5 c | 10.5 cd | 5.5 c | 5.0 de |
| Georgia-SP/RKN | 1.2 c | 2.3 c | 6.8 d | 4.7 c | 3.6 e |
| CV % | 31.5 | 46.9 | 30.1 | 26.2 | 34.0 |

†Values within columns followed by the same letter are not different at Waller-Duncan kratio = 100.

Example 5

TSMK, Seed Count, Plant Stand Visual Rating, and Seedling Vigor

Total sound mature kernel percentage (TSMK) was highest for Georgia-SP/RKN and Georgia-17SP (Table 5). Seed size of Georgia-SP/RKN is similar to Georgia-17SP, and both are significantly larger than the other spanish cultivars tested resulting in a significantly lower seed count $kg^{-1}$. Visual stand ratings and visual seedling vigor ratings were evaluated two weeks after planting. Both ratings utilize a 1-9 rating scale with 1 being poor and 9 being the highest. Georgia-SP/RKN exhibited improved visual stand ratings and seedling vigor ratings compared to Georgia-17SP, but Tamnut OL06 and OLé had the highest visual ratings for stand and seedling vigor overall.

Example 6

Multi-Trait Comparison of Georgia-17SP and Georgia-SP/RKN

From 2018 to 2021, Georgia-SP/RKN and Georgia-17SP were grown together in five trials that included sister lines of Georgia-SP/RKN at the Gibbs Research Farm and Blackshank Research Farm in Tifton, GA under both nematode-free and nematode-infested conditions, respectively (Table 6). Pod Yield, dollar value, TSWV, and total disease (TD) were evaluated as described above. Under moderate leaf scorch (LSC) pressure, cultivars usually show homogeneous symptoms throughout the plot, therefore we have adopted a 1-9 visual rating scale where 1 equals no symptoms, 5 equals ~50% symptomatic leaves, and 9 equals all leaves symptomatic. Visual rating of LSC was carried out when clear symptoms were present and consistent across the trial, usually at the same time as TSWV or TD ratings. TSWV was evaluated for all 5 trials while pod yield, dollar value, TD, and LSC were evaluated at 4 out of the 5 experiments. Pod yield, dollar value, TSWV, and TD were not significantly different, but leaf scorch (LSC) did differ significantly for these cultivars, with Georgia-SP/RKN having higher visual LSC symptoms.

TABLE 6

Multi-environment head-to-head comparison of Georgia-17SP to Georgia-SP/RKN for pod yield, dollar value, tomato spotted wilt virus, total disease, and leaf scorch at Tifton, GA from 2018 to 2021.

| Cultivar | Pod Yield † | Dollar value | TSWV‡ | TD | LSC |
|---|---|---|---|---|---|
| | kg/ha | $/ha | % | % | 1-9 scale |
| Georgia-17SP | 4697§ | 1878 | 6.6 | 17.1 | 4.4 b |
| Georgia-SP/RKN | 4450 | 1783 | 8.0 | 14.6 | 6.6 a |

† Pod yield, Dollar Value, TD, and LSC was evaluated in 4 environments between 2018-2021; TSWV was evaluated in 5 environments between 2018-2020.
‡TSWV, incidence of tomato spotted wilt virus as a percentage of total plot length evaluated ~70 days after planting; TD, total disease score expressed as a percentage of total plot length evaluated ~140 DAP, with TSWV usually the primary disease present; LSC, leaf scorch/pepper spot disease symptoms rated from low to high incidence on a 1-9 scale.
§Values within columns followed by the same letter are not different at Waller-Duncan kratio = 100

Example 7

Shelling Outturn

Shelling outturn data from the April-planted spanish market type yield trials in 2020 and 2021 revealed no significant difference between Georgia-SP/RKN and Georgia-17SP for Jumbo (8.33 mm by 19.05 mm screen), Medium (<8.33 mm and ≥7.14 mm by 19.05 mm screen), or Number 1 (<7.14 mm and ≥5.95 mm by 19.05 mm) spanish seed size fractions, other kernels (OK), damaged kernels (DK), or percent meat (Table 7). Georgia-SP/RKN, did however, exhibit significant differences for several shelling characteristics compared to other spanish cultivars. Seed size distribution was generally larger than the other spanish market types, with Georgia-SP/RKN exhibiting the largest percentage of Jumbo seeds (29.2%). The percentage of Mediums was not different than Tamnut OL06, OLé, or OLin, and percentage of No. 1 kernels was lower than Georgia-04S, Georgia Browne, Tamnut OL06, OLé, and OLin. Georgia-SP/RKN was among the lowest for OK and DK percentages. Percent meat was highest for Georgia-SP/RKN and Georgia-17SP.

TABLE 7

Two-year average shelling outturn of Georgia-SP/RKN compared to six spanish market type peanut cultivars in 2020 and 2021 at Tifton, GA.

| Cultivar | Jumbo† % | Med. % | No. 1 % | OK % | DK % | Meat % |
|---|---|---|---|---|---|---|
| Georgia-17SP | 28.6 a‡ | 49.4 b | 5.5 e | 2.5 b | 0.00 b | 78.0 a |
| Georgia-SP/RKN | 29.2 a | 48.5 b | 5.8 e | 2.3 b | 0.00 b | 79.1 a |
| Georgia-04S | 7.3 cd | 62.0 a | 19.2 d | 3.1 b | 0.00 b | 75.8 b |
| Georgia Browne | 4.6 d | 59.1 a | 25.4 c | 3.0 b | 0.00 b | 76.1 b |
| Tamnut OL06 | 12.4 b | 48.1 b | 29.3 bc | 5.5 a | 0.03 ab | 67.8 d |
| OLé | 9.6 bc | 48.5 b | 32.2 b | 5.6 a | 0.00 b | 69.9 c |
| OLin | 4.9 d | 44.3 b | 38.4 a | 6.5 a | 0.05 a | 70.7 c |

†Jumbo, jumbo kernels ≥8.33 mm by 19.05 mm screen; Med., medium kernels <8.33 mm and ≥7.14 mm by 19.05 mm screen; No. 1, Number 1 kernels <7.14 mm and ≥5.95 mm by 19.05 mm screen; OK, percentage of other kernels; DK, percentage of damaged kernels; Meat, percent meat; Hull, percent hull.
‡Values within columns followed by the same letter are not different at Waller-Duncan kratio = 100.

Example 8

Pod Size Distribution

Pod size distributions were not significantly different between Georgia-SP/RKN and Georgia-17SP in 2020 and 2021, indicating highly similar pod characteristics (Table 8). There were no significant differences for percentage of pod width>15.1 mm (Red Pan). Tamnut OL06 and OLé had the highest percentage of pod widths from 15.1 mm to 13.5 mm (White Pan) and the lowest percentages less than 13.5 mm (Blue Pan). The other cultivars, including Georgia-SP/RKN, were not significantly different. Weight of 100 pods was highest for Georgia-SP/RKN, Georgia-17SP, and Tamnut OL06. While Georgia-SP/RKN and Georgia-17SP had smaller pod size distributions than Tamnut OL06, the pods for these three cultivars were of similar weight.

TABLE 8

Two-year average pod presizer distribution of Georgia-SP/RKN and Georgia-17SP in 2020 and 2021 at Tifton, GA.

| Cultivar | Red Pan >15.1 mm | White Pan 15.1 mm to 13.5 mm | Blue Pan <13.5 mm | 100 Pod Wt. |
|---|---|---|---|---|
| | % | % | % | g/100 pods |
| Georgia-17SP | 0.1 | 0.7 c | 99.2 a | 122.4 ab |
| Georgia-SP/RKN | 0.1 | 2.8 c | 97.1 a | 125.0 a |
| Georgia-04S | 0.2 | 0.8 c | 99.0 a | 101.2 c |
| Georgia Browne | 0.2 | 0.3 c | 99.6 a | 99.8 cd |
| Tamnut OL06 | 0.2 | 12.4 a | 87.4 c | 119.6 ab |
| OLé | 0.1 | 8.0 b | 92.0 b | 114.5 b |
| OLin | 0.0 | 1.3 c | 98.7 a | 91.8 d |

† Values within columns followed by the same letter are not different at Waller-Duncan kratio = 100.

Example 9

Roasted Peanut Flavor

Roasted peanut flavor was evaluated by a flavor analysis sensory panel on peanuts grown in the same trial in 2018 at Tifton, GA, revealing no significant differences for flavor attributes (Table 9). Ratio of oleic to linoleic fatty acid was not significantly different than Georgia-17SP, indicating that both have the high oleic trait. Blanchability analysis, however, revealed significantly lower rednose percentage for Georgia-SP/RKN compared to Georgia-17SP, with 2.7% vs. 7.5%, respectively. Other blanching characteristics were not significantly different.

TABLE 9

Average roasted flavor sensory ratings, oleic: linoleic fatty acid ratio, and blanching characteristics of Georgia-SP/RKN compared to Georgia-17SP, grown in 2018 at Tifton, GA.

| Cultivar | Roasted "Peanutty" Flavor | O/L Ratio | Blanchability (%) Blanched | Rednose | Unblanched |
|---|---|---|---|---|---|
| Georgia-17SP | 5.1 a† | 32.2 a | 90.8 a | 7.5 a | 1.6 a |
| Georgia-SP/RKN | 5.2 a | 31.2 a | 95.5 a | 2.7 b | 1.8 a |

†Values within columns followed by the same letter are not different at Waller-Duncan kratio = 100.
‡ RP Flavor Score = 1-10 scale, where >5.0 is considered a good roasted "peanutty" flavor.

Example 10

RKN Resistance

Field testing for resistance to RKN was conducted in 2019 in Tifton and Attapulgus, GA to confirm results from marker-assisted selection. Georgia-SP/RKN was tested along with sister lines, and comparison cultivars, Georgia-17SP, and Georgia-04S. Data for the sister lines included in the trial are not shown here. Georgia-04S is susceptible to RKN, Georgia-17SP is partially resistant to RKN, and Georgia-SP/RKN is highly resistant to RKN (Table 10). Georgia-SP/RKN had significantly lower RKN count, visual root galling percentage, and visual pod galling percentage than both Georgia-04S and Georgia-17SP. Pod yield was not significantly different under heavy RKN pressure between Georgia-SP/RKN and Georgia-17SP. Georgia-04S had significantly lower pod yield than both Georgia-SP/RKN and Georgia-17SP under heavy RKN pressure.

Table 10A and 10B. Root-knot nematode counts and visual gall ratings of Georgia-SP/RKN, Georgia-04S and Georgia-17SP at Attapulgus (Table 10A) and Tifton (Table 10B), GA in 2019.

TABLE 10A

| Cultivar | RKN Count† | Visual Gall Rating (0-100%) Root | Pod | Pod Yield |
|---|---|---|---|---|
| | no./100 cm$^3$ | % | % | kg/ha |
| Georgia-04S | 867 a‡ | 53.3 a | 60.0 a | 3825 b |
| Georgia-17SP | 294 b | 26.7 b | 10.5 b | 6836 a |
| Georgia SP/RKN | 57 c | 0.0 c | 0.0 b | 6782 a |

TABLE 10B

| Cultivar | RKN Count† | Visual Gall Rating (0-100%) Root | Pod | Pod Yield |
|---|---|---|---|---|
| | no./100 cm$^3$ | % | % | kg/ha |
| Georgia-04S | 93 | 12.5 a | — | 4015 b |
| Georgia-17SP | 136 | 6.5 ab | — | 5941 a |
| Georgia-SP/RKN | 0 | 0.3 b | — | 5507 a |

†RKN count, number of J2 stage root-knot nematodes in 100 cm$^3$ soil; Visual Gall Ratings, visual estimations of percentage of plant material affected by galling caused by root-knot nematode.
‡ Values within columns followed by the same letter are not different at Waller-Duncan kratio = 100.

Example 11

Mature Plant Height

Mature plant height was measured at 2 locations in 2021. Georgia-04S and Georgia Browne were the tallest (44.4 and 44.1 cm, respectively), Georgia-17SP was the shortest (40.7 cm), and Georgia-SP/RKN was intermediate to these cultivars at 42.4 cm (Table 11). Length and width of leaflets was also measured at 2 locations in 2021. Leaflet lengths did not differ significantly, however, Georgia-SP/RKN and Georgia-17SP did have more narrow leaves (2.1 cm) than Georgia Browne and Georgia-04S (2.4 cm).

TABLE 11

Mature plant height at the mainstem, mature leaflet length and width at the extremes. Data collected at UGA's Gibbs Research Farm and RDC Center Farm at Tifton, GA in 2021.

| | Height | Leaflet Length | Width |
|---|---|---|---|
| | cm | cm | cm |
| Georgia-SP/RKN | 42.4 b | 5.5 | 2.1 b |
| Georgia-17SP | 40.7 c | 5.6 | 2.1 b |
| Georgia-04S | 44.4 a | 5.5 | 2.4 a |
| Georgia Browne | 44.1 a | 5.6 | 2.4 a |
| CV | 3.5 | 4.0 | 6.6 |

Example 12

Production of 'Georgia-SP/RKN' Plants

'Georgia-SP/RKN' can be grown under normal conditions for growing peanuts, and bulk seed for large-scale planting can be obtained by methods known in certified seed production. For example, bulk seed may be produced by planting 'Georgia-SP/RKN' seeds (such as those obtained from ATCC Accession No: PTA-127584 (NPGS PI No. PI #700991)), allowing the mature plants to produce seed by self-pollination and then collecting the seed. Standard precautions should be taken to prevent cross-pollination from other peanut plants, such as growing the variety in an isolated plot of sterilized soil, removing adjacent vegetation, etc. The 'Georgia-SP/RKN' seeds deposited with ATCC and NPGS are breeder seeds; propagation of plants from these seeds can be performed under standard conditions.

Example 13

Introducing Traits of 'Georgia-SP/RKN' into Other Peanut Varieties

The morphological and physiological characteristics of 'Georgia-SP/RKN', including resistance to diseases that affect peanuts (including RKN and TSV), such as RKN resistance (in some embodiments with about 3% or less of the TxAG-6 introgression on chromosome A09), and in some examples one or more of high oleic fatty acid concentration in seed oil, TSV resistance, high percentage of total sound mature kernels (TSMK), high pod yield compared to other spanish market type cultivars, small percentage of large fancy pods (e.g., 13.49 mm size distribution), high percentage of total meat content, large spanish market type seed size distribution, large percentage of spanish jumbo and medium seeds, medium plus maturity, runner growth habit, dark green foliage, and tan seedcoat (testa) color, or combinations thereof, can be introduced into other peanut varieties (such as other peanut cultivars) by conventional breeding techniques.

For example, 'Georgia-SP/RKN' can be grown in pollination proximity to another variety of peanut, allowing cross-pollination to occur between 'Georgia-SP/RKN' and the other variety, and then harvesting the hybrid seeds. Plants grown from these hybrid seeds can then be tested for the maintenance of the characteristics described herein for 'Georgia-SP/RKN' (such as one or more of such as RKN resistance (in some embodiments with about 3% or less of the TxAG-6 introgression in chromosome A09), and in some examples one or more of high oleic fatty acid concentration in seed oil, TSWV resistance, high percentage of total sound mature kernels (TSMK), high pod yield, small percentage of large fancy pods (e.g., 13.49 mm size distribution), high percentage of total meat content, large spanish type seed size distribution, large percentage of spanish type jumbo and medium seeds, medium plus maturity, runner growth habit, dark green foliage, and tan seedcoat (testa) color; or combinations thereof), and/or the plants can simply be observed to see if they display the same characteristics of 'Georgia-SP/RKN', such as those described in Tables 1-11.

For example, plants grown from these hybrid seeds can be tested for any of the morphological characteristics described herein, for example such as RKN resistance (in some embodiments with about 3% or less of the TxAG-6 introgression in chromosome A09), and in some examples one or more of high oleic fatty acid concentration in seed oil, TSWV resistance, high percentage of total sound mature kernels (TSMK), high pod yield, small percentage of large fancy pods (e.g., 13.49 mm size distribution), high percentage of total meat content, large spanish type seed size distribution, large percentage of spanish type jumbo and medium seeds, medium plus maturity, runner growth habit, dark green foliage, and tan seedcoat (testa) color, or combinations thereof.

In this way, such as RKN resistance (in some embodiments with about 3% or less of the TxAG-6 introgression in chromosome A09), and in some examples one or more of high oleic fatty acid concentration in seed oil, TSWV resistance, high percentage of total sound mature kernels (TSMK), high pod yield, small percentage of large fancy pods (e.g., 13.49 mm size distribution), high percentage of total meat content, large spanish type seed size distribution, large percentage of spanish jumbo and medium seeds, medium plus maturity, runner growth habit, dark green foliage, and tan seedcoat (testa) color, or combinations thereof, may be combined with other desirable plant characteristics. Thus, the provision of 'Georgia-SP/RKN' enables the production of progeny plants of 'Georgia-SP/RKN' having one or more of such as RKN resistance (in some embodiments with about 3% or less of the TxAG-6 introgression in chromosome A09), and in some examples one or more of high oleic fatty acid concentration in seed oil, TSWV resistance, high percentage of total sound mature kernels (TSMK), high pod yield, small percentage of large fancy pods (e.g., 13.49 mm size distribution), high percentage of total meat content, large spanish type seed size distribution, large percentage of spanish jumbo and medium seeds, medium plus maturity, runner growth habit, dark green foliage, large runner seed size, and tan seedcoat (testa) color, and combinations thereof.

"Progeny plants" of 'Georgia-SP/RKN' are any plants that are the offspring of a cross between 'Georgia-SP/RKN' and any other plant or plants. Progeny plants also include successive generations of the offspring, for example those selected for TSWV resistance, high yield, and a high percentage of TSMKs. First-generation progeny plants may retain the properties of the 'Georgia-SP/RKN' parent (such as TSWV resistance, high yield, and a high percentage of TSMKs). However, if a first-generation progeny plant does not retain the characteristics observed with 'Georgia-SP/RKN' (such as TSWV resistance, high yield, and a high percentage of TSMKs), subsequent generations of offspring can be recycled for those which have at least the same TSWV resistance, yield, and percentage of TSMKs as does 'Georgia-SP/RKN' described herein. In one embodiment, subsequent generations of offspring can have TSWV resistance, leaf scorch susceptibility caused by the fungus *Leptosphaerulina crassiasca* (Séchet) Jackson and Bell, yield, and percentage of TSMKs similar to that or even that exceed that of 'Georgia-SP/RKN'.

In addition, 'Georgia-SP/RKN' can be used as transformation targets for the production of transgenic peanuts. In certain embodiments, the present disclosure contemplates the transformation of cells derived from 'Georgia-SP/RKN' with at least one transgene. For example, transgenes that can be used, include, but are not limited to, transgenes that confer: resistance to one or more of herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination, abiotic stress tolerance, modified phosphorus content, modified antioxidant content; modified essential seed amino acid content, modified fatty acid content, modified carbohydrate content, modified peanut fiber content, low pod-splitting, modified seed yield, modified oil percent, modified protein percent, modified fancy pod percent, modified pod size, modified pod shape, and modified pod color. Examples of such genes and methods of transforming plants are described in U.S. Pat. No. 6,025,545.

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

We claim:

1. A seed of peanut variety 'Georgia-SP/RKN', wherein a representative sample of seed of the variety has been deposited under American Type Culture Collection (ATCC) Accession No. PTA-127584.

2. A seed mixture, comprising the seed of claim 1.

3. A peanut plant of peanut variety 'Georgia-SP/RKN' grown from a seed of claim 1.

4. A plant part of the peanut plant of claim 3.

5. The plant part of claim 4, wherein the plant part is pollen, an ovule or a cell.

6. A tissue culture produced from protoplasts or cells from the peanut plant of claim 3.

7. The tissue culture of claim 6, wherein the cells or protoplasts are produced from a leaf, stem, protoplast, pollen, ovule, embryo, cotyledon, hypocotyl, meristematic cell, root, root tip, pistil, anther, flower, seed, shoot, stem, pedicel, pod or petiole.

8. A peanut plant regenerated from the tissue culture of claim 6, wherein the peanut plant comprises all of the morphological and physiological properties of a peanut plant grown from a seed deposited under ATCC Accession No. PTA-127584.

9. A method of producing peanut seed, consisting of:

self-pollinating the peanut plant of claim 3 or crossing the peanut plant of claim 3 with a second peanut plant; and harvesting a resulting peanut seed.

10. A progeny peanut seed produced by the method of claim 9.

11. A progeny peanut plant, or a part thereof, produced by growing the seed of claim 10.

12. The method of claim 9, wherein the second peanut plant is transgenic.

13. An $F_1$ hybrid seed produced by the method of claim 9.

14. A method of introducing a desired trait into peanut variety 'Georgia-SP/RKN' comprising:

(a) crossing the plant of claim 3 with a second plant comprising a desired trait to produce $F_1$ progeny plants;

(b) selecting $F_1$ progeny plants that have the desired trait to produce selected $F_1$ progeny plants;

(c) crossing the selected progeny plants with at least a first plant of variety 'Georgia-SP/RKN' to produce backcross progeny plants;

(d) selecting backcross progeny plants that are resistant to tomato spotted wilt caused by Tomato Spotted Wilt Virus (TSWV) and peanut root-knot nematode [*Meloidogyne arenaria* (Neal)] (RKN), to produce selected backcross progeny plants; and (e) repeating steps (c) and (d) one or more times in succession to produce selected second or higher backcross progeny plants that comprise the resistance to tomato spotted wilt caused by Tomato Spotted Wilt Virus (TSWV) and peanut root-knot nematode [*Meloidogyne arenaria* (Neal)] (RKN) of 'Georgia-SP/RKN' when grown in the same environmental conditions.

15. The method of claim 14, wherein the desired trait comprises one or more of herbicide tolerance, resistance to an insect, resistance to a bacterial disease, resistance to a viral disease, resistance to a fungal disease, resistance to a nematode, resistance to a pest, male sterility, abiotic stress tolerance, modified phosphorus content, modified antioxidant content, modified essential seed amino acid content, modified fatty acid content, modified carbohydrate content, modified peanut fiber content, seed-splitting, modified seed yield, modified oil percent, modified protein percent, modified fancy pod percent, modified pod size, modified pod shape, or modified pod color.

16. The plant of claim 3, further comprising a single locus conversion.

17. A method of producing a hybrid peanut plant derived from peanut variety 'Georgia-SP/RKN', comprising:

(a) preparing a progeny plant derived from peanut variety 'Georgia-SP/RKN' ATCC Accession No. PTA-127584 by crossing the plant of claim 3 with a peanut plant of a second variety;

(b) self-pollinating the progeny plant for crossing the progeny plant with a second plant to produce a seed of a progeny plant of a subsequent generation;

(c) growing a progeny plant of a subsequent generation from said seed and crossing the progeny plant of a subsequent generation with itself or a second plant; and (d) repeating steps (b) and (c) for an additional 3-10 generations to produce a hybrid peanut plant derived from the peanut variety 'Georgia-SP/RKN'.

18. A $F_1$ plant that is the progeny plant produced in part (a) of claim 17 plant.

19. A progeny peanut seed produced by the method of claim 9, wherein a progeny peanut plant resulting from the progeny peanut seed comprises all of the morphological and physiological properties of a peanut plant grown from a seed deposited under ATCC Accession No. PTA-127584.

* * * * *